(12) United States Patent
Swanson et al.

(10) Patent No.: US 11,681,093 B2
(45) Date of Patent: Jun. 20, 2023

(54) MULTICORE FIBER WITH DISTAL MOTOR

(71) Applicants: Eric Swanson, Gloucester, MA (US); Anthony Kam, Arlington, MA (US)

(72) Inventors: Eric Swanson, Gloucester, MA (US); Anthony Kam, Arlington, MA (US)

(73) Assignee: Eric Swanson, Gloucester, MA (US)

( * ) Notice: Subject to any disclaimer, the term of this patent is extended or adjusted under 35 U.S.C. 154(b) by 274 days.

(21) Appl. No.: 16/865,454

(22) Filed: May 4, 2020

(65) Prior Publication Data
US 2021/0341668 A1      Nov. 4, 2021

(51) Int. Cl.
*A61B 1/00*      (2006.01)
*A61B 1/07*      (2006.01)
(Continued)

(52) U.S. Cl.
CPC ........ *G02B 6/02042* (2013.01); *A61B 1/0016* (2013.01); *A61B 1/00096* (2013.01); *A61B 1/00167* (2013.01); *A61B 1/00172* (2013.01); *A61B 1/00177* (2013.01); *A61B 1/07* (2013.01); *A61B 3/10* (2013.01); *A61B 5/0066* (2013.01); *A61B 5/0084* (2013.01);
(Continued)

(58) Field of Classification Search
CPC .............. A61B 1/00096; A61B 1/0016; A61B 1/00167; A61B 1/00172; A61B 1/00177; A61B 1/07; A61B 3/10; A61B 5/0084; A61B 5/02007; A61B 5/6852; G01B 9/02091; G02B 6/02042
See application file for complete search history.

(56) References Cited

U.S. PATENT DOCUMENTS

| 5,212,743 A | 5/1993 | Heisman |
| 5,321,501 A | 6/1994 | Swanson |

(Continued)

FOREIGN PATENT DOCUMENTS

| EP | 0981733 | 11/2004 |
| EP | 0883793 | 11/2007 |

(Continued)

OTHER PUBLICATIONS

Chao Zhou, et al.. Space-division multiplexing optical coherence tomography, Optics Express, Aug. 6, 2013, pp. 19219-19227 vol. 21, No. 16, DOI:10.1364/OE.21.019219.
(Continued)

*Primary Examiner* — Ryan A Lepisto
(74) *Attorney, Agent, or Firm* — Rauschenbach Patent Law Group, PLLC; Kurt Rauschenbach

(57) ABSTRACT

An optical probe imaging system includes an optical probe having a multicore optical fiber. Distal optics image light propagating in the multicore optical fiber so as to generate a light pattern on a sample that is based on a relative position of the cores. A distal motor causes the light pattern to traverse a path across the sample. An optical receiver includes a first receiver receiving light that has traversed the path across the sample from one of the at least two cores and a second receiver receiving light that has traversed the path across the sample from the other of the cores, such that the first receiver and the second receiver detect light in parallel. A processor maps relative position of the cores at the distal facet based on signals generated by the receiver.

18 Claims, 10 Drawing Sheets

(51) Int. Cl.
  *A61B 3/10* (2006.01)
  *A61B 5/00* (2006.01)
  *A61B 5/02* (2006.01)
  *G02B 6/02* (2006.01)
  *G01B 9/02091* (2022.01)

(52) U.S. Cl.
  CPC ........ *A61B 5/02007* (2013.01); *A61B 5/6852* (2013.01); *G01B 9/02091* (2013.01)

(56) References Cited

U.S. PATENT DOCUMENTS

| | | |
|---|---|---|
| 5,459,570 A | 10/1995 | Swanson |
| 5,465,147 A | 11/1995 | Swanson |
| 5,956,355 A | 9/1999 | Swanson |
| 6,134,003 A | 10/2000 | Tearney |
| 6,160,826 A | 12/2000 | Swanson |
| 6,191,862 B1 | 2/2001 | Swanson |
| 6,288,784 B1 | 10/2001 | Hitzenberger |
| 6,445,939 B1 | 9/2002 | Swanson |
| 6,485,413 B1 | 11/2002 | Boppart |
| 6,501,551 B1 | 12/2002 | Tearney |
| 6,564,087 B1 | 5/2003 | Pitris |
| 6,947,648 B2 | 2/2005 | Swanson |
| 6,891,984 B2 | 5/2005 | Peterson |
| 7,061,618 B2 | 6/2006 | Atia et al. |
| 7,530,948 B2 | 5/2009 | Seibel |
| 7,843,572 B2 | 11/2010 | Tearney et al. |
| 7,864,822 B2 | 1/2011 | Bouma |
| 7,916,387 B2 | 3/2011 | Schmitt |
| 8,078,245 B2 | 12/2011 | Daly |
| 8,384,909 B2 | 2/2013 | Yun |
| 8,416,818 B2 | 4/2013 | Bouma |
| 8,437,007 B2 | 5/2013 | Flanders |
| 8,515,221 B2 | 8/2013 | Flanders |
| 8,690,330 B2 | 4/2014 | Hacker et al. |
| 8,711,364 B2 | 4/2014 | Brennan |
| 8,854,629 B2 | 10/2014 | Frisken |
| 8,994,954 B2 | 3/2015 | Minneman |
| 9,008,142 B2 | 4/2015 | Minneman |
| 9,044,164 B2 | 6/2015 | Hacker et al. |
| 9,162,404 B2 | 10/2015 | Doerr |
| 9,400,169 B2 | 7/2016 | Zhou |
| 9,464,883 B2 | 10/2016 | Swanson et al. |
| 9,683,928 B2 | 6/2017 | Swanson |
| 10,107,616 B2 | 10/2018 | Zhou |
| 10,126,572 B2 | 11/2018 | Zhang et al. |
| 10,132,610 B2 | 11/2018 | Swanson et al. |
| 10,191,145 B2 | 1/2019 | Swanson |
| 10,401,883 B2 | 9/2019 | Swanson et al. |
| 10,416,288 B2 | 9/2019 | Swanson |
| 10,895,525 B2 | 1/2021 | Swanson |
| 10,907,951 B2 | 2/2021 | Avci |
| 10,969,571 B2 | 4/2021 | Swanson |
| 2006/0187537 A1 | 8/2006 | Huber et al. |
| 2011/0218404 A1 | 9/2011 | Hirakawa |
| 2012/0002971 A1 | 1/2012 | Doerr |
| 2012/0099112 A1 | 4/2012 | Alphonse et al. |
| 2012/0224165 A1 | 9/2012 | Swanson |
| 2012/0226118 A1 | 9/2012 | Delbeke et al. |
| 2013/0044974 A1 | 2/2013 | Doerr |
| 2013/0209022 A1 | 8/2013 | Doerr |
| 2014/0126902 A1 | 5/2014 | Swanson |
| 2014/0126990 A1 | 5/2014 | Swanson |
| 2014/0147079 A1 | 5/2014 | Doerr |
| 2014/0160488 A1 | 6/2014 | Zhou |
| 2014/0235948 A1 | 8/2014 | Mahalati et al. |
| 2014/0376000 A1 | 9/2014 | Swanson |
| 2014/0376001 A1 | 12/2014 | Swanson |
| 2016/0231101 A1 | 8/2016 | Swanson et al. |
| 2016/0299170 A1* | 10/2016 | Ito .................... G02B 23/26 |
| 2016/0035700 A1 | 12/2016 | Swanson |
| 2016/0357007 A1* | 12/2016 | Swanson ............ G01B 9/02028 |
| 2017/0143196 A1 | 5/2017 | Liang et al. |
| 2017/0205253 A1 | 7/2017 | Handerek |

FOREIGN PATENT DOCUMENTS

| | | |
|---|---|---|
| EP | 1839375 | 4/2014 |
| WO | 2012088361 | 6/2012 |
| WO | 2014/088650 | 6/2014 |
| WO | 2014/089504 | 6/2014 |

OTHER PUBLICATIONS

Yongyan Huang, et al., Wide-field high-speed space-division multiplexing optical coherence tomography using an integrated photonic device, Biomedical Optics Express, Jul. 28, 2017, pp. 3856-3867, vol. 8, No. 8, DOI:10.1364/BOE.8.003856.

Hitzenberger, Christoph K., et at., In Vivo Intraocular Ranging By Wavelength Tuning Interferometry, SPIE, pp. 47-51, vol. 3251, retrieved from: http://proceedings.spiedigitallibrary.org/ on Sep. 24, 2013.

Warren L. Stutzman and Gary A. Thiele, "Antena Theory and Design", John Wiley & Sons, ISBN 0-471-04458-X, 1981. Textbook.

Y. Zhao, Z. Chen, C. Saxer, S. Xiang, J.F. de Beor, and J.S. Nelson, "Phase-resolved optical coherence tomography and optical Doppler tomography for imaging blood flow in human skin with fast scanning speed and high velocity sensitivity," Opt. Lett. 25(2), 114-116 (2000).

W. Choi, B. Potsaid, V. Jayaraman, B. Baumann, I. Grulkowski, J. J. Liu, C. D. Lu, A. E. Cable, D. Huang, J. S. Duker, and J. G. Fujimoto, "Phase sensitive swept-source optical coherence tomography imaging of the human retina with a vertical cavity surface-emiting laser light source," Opt. Lett. 38(3), 338-340 (2013).

Youxin Mao, Costel Flueraru, Shoude Chang, Dan P. Popescu, Michael G. Sowa, "Preormance analysis of a swept-source optical coherence tomography system with a quadrature interferometer and optical amplification", Optics Communications, vol. 284, Issues 10-11, May 15, 2011.

C.M. Eigenwillig, B. R. Biedermann, G. Palte, and R. Huber, "K-space linear Fourier domain mode locked laser and applications for optical coherence tomography," Optics Express 16(12), 8916-8937 (2008).

Yizheng Zhu, Neil G. Terry, and Adam Wax, "Scanning fiber angle-resolved low coherence interferometry", Optics Letters, vol. 34, No. 20, 2009.

Michael Giacomelli, Yizheng, Zhu, John Lee, Adam Wax, "Size and shape determination of spheroidal scatters using two-dimensional angle resolved scattering",Optics Express, vol. 18, No. 14, 2010.

Humle, J.C. et al., "Fully integrated hybrid silicon free-space beam steering source with 32 channel phased array" International Society for Optics and Photonics (SPIE PW), San Francisco, CA Feb. 1-6, 2014, pp. 898907-1-898907-15.

Kevin Gourley, Ilya Golu, Brahim Chebbi, "First experimental demonstration of a Fresnel Axicon", Proceedings of the SPIE, doi:10.1117/12.807162, Jun. 18, 2008.

Oto Brzobohatý, TomášČižmár, and Pavel Zemánek, "High quality quasi-Bessel beam generated by round-tip axicon", Optics Express, vol. 16, No. 17, 2008.

S. Yerolatsitis, I. Gris-Sánchez, T. A. Birks, "Tapered Mode Multiplexers for Single Mode to Multi Mode Fibre Mode Transitions", Proceedings of the Optical Fiber Communications Conference, Paper w3B.4, 2015.

A. M. Velazquez-Benitez, J. C. Alvarado, G. Lopez-Galmiche, J. E. Antonio-Lopez, J. Hernández-Cordero, J. Sanchez-Mondragon, P. Sillard, C. M. Okonkwo, and R. Amezcua-Correa, "Six mode selective fiber optic spatial multiplexer", Optics Letters, vol. 40, No. 8, Apr. 15, 2015.

Bernard Oduro, Rand Ismaeel, Timothy Lee and Gilberto Brambilla, "Selective Excitation of High Order Modes in Few Mode Fibres Using Optical Microfibres", Proceedings of the Optical Fiber Communications Conference, Paper M3D.5, 2015.

S. U. Alam*, Y. Jung, Q. Kang, F. Poletti, J.K. Sahu and D. J. Richardson, "Recent Progress in the Development of Few Mode Fiber Amplifiers", Proceedings of the Optical Fiber Communications Conference, Paper Tu3C.1, 2015.

(56) References Cited

OTHER PUBLICATIONS

R. Ryf, N. K. Fontaine1, M. Montoliu, S. Randel1, B. Ercan, H. Chen, S. Chandrasekhar, A. H. Gnauck, S. G. Leon-Saval, J. Bland-Hawthorn, J. R. Salazar-Gil, Y. Sun, R. Lingle, Jr., "Photonic-Lantern-Based Mode Multiplexers for Few-Mode-Fiber Transmission", Proceedings of the Optical Fiber Communications Conference, Paper W4J.2., 2015.
Sergio G. Leon-Saval, Nicolas K. Fontaine, Joel R. Salazar-Gil, Burcu Ercan, Roland Ryf, and Joss Bland-Hawthorn, "Mode-selective photonic lanterns for space division multiplexing", Optics Express, vol. 22, No. 1 Jan. 13, 2014.
Haoshuo Chen, Nicolas K. Fontaine, Roland Ryf, Binbin Guan, S. J. Ben Yoo, and Ton (A. M. J.) Koonen, "Design Constraints of Photonic-Lantern Spatial Multiplexer Based on Laser-Inscribed 3-D Waveguide Technology", Journal of Lightwave Technology, vol. 33, No. 6, Mar. 15, 2015.
Haoshuo Chen, Roy van Uden, Chigo Okonkwo, and Ton Koonen, "Compact spatial multiplexers for mode division multiplexing", Optics Express, vol. 22, No. 26, Dec. 26, 2014.
Simon Schneider, Matthias Lauermann, Philipp-Immanuel Dietrich, Claudius Weimann, Wolfgang Freude, and Christian Koos, Optical coherence tomography system mass producible on a silicon photonic chip, Optics Express, vol. 24, No. 2, Jan. 2016.
Eduardo Margallo-Balb'as, Gregory Pandraud and Patrick J. French, "Miniature Optical Coherence Tomography System Based on Silicon Photonics", SPIE 2Proceedings, vol. 6847 (2008).
Christopher R. Doerr and Lawrence L. Buhl, "Circular Grating Coupler for Creating Focused Azimuthally and Radially Polarized Beams", Optics Letters, vol. 36, No. 7, Apr. 1, 2011.
Nenad Bozinovic, Yang Yue, Yongxiong Ren, Moshe Tur, Poul Kristensen, Hao Huang, Alan E. Willner, Siddharth Ramachandran, "Terabit-Scale Orbital Angular Momentum Mode Division Multiplexing in Fibers", Science Magazine, vol. 340 Jun. 28, 2013.
D. Huang. E. A. Swanson, C. P. Lin, J. S. Schuman, W. G. Stinson, W. Chang, M. R. Hee, t. Flotte, K. Gregory, C. A. Puliafito and J. G. Fujimoto, "Optical coherence tomography," Science 254(5035), 1178-1181 (1991).
R. Leitgeb, C. Hitzenberger, and A. Fercher, "Performance of fourier domain vs. time domain optical coherence tomography," OPt. Express 11(8), 889-894 (2003).
J. F. de Boer, B. Cense, B. H, Park, M. C. Pierce, G. J. Tearney, and B. E. Bouma, "Improved signal-to-noise ratio in spectral-domain compared with time-domain optical coherence tomography," Opt. Lett. 28(21), 2067-2069 (2003).
M. Choma, M. Sarunic, C. Yang, and J. Izatt, "Sensitvity advantage of swept source and fourier domain optical coherence tomography," Opt. Express 11(18), 2183-2189 (2003).
M. Wojtkowski, A, Kowalczyk, R. Leitgeb, and A. F. Fercher, "Full range complex spectral optical coherence tomography technique in eye imaging," Opt. lett. 27(16), 1415-1417 (2002).
A. F. Fercher, C. K. Hitzenberger, G. Kamp, and S. Y. El-Zaiat, "Measurement of intraocular distances by backsattering spectral interferometry," Opt. Commun. 117(1), 43-48 (1995).
S. R. Chinn, E. A. Swanson, and J. G. Fujimoto, "Optical cohoerence tomography using a frequency-tunable optical source," Opt. Lett. 22(5), 340-342 (1997).
S. Yun, G. Tearney, J. de Boer, N. Iftima, and B. Bouma, "High-speed optical frequency-domain imaging," Opt. Express 11(22), 2953-2963 (2003).
R. Huber, M. Wojtkowski, and J.G. Fujimoto, "Fourier Domain Mode Locking (FDML): A new laser operating regime and applications for optical coherence tomography," Opt. Express 14(8), 3225-3237 (2006).
R. Huber, D. C. Adler, and J. G, Fujimoto, "Buffered Fourier domain mode locking: unidirectional swept laser sources for optical coherence tomography imaging at 370,000 lines/s," Opt. Lett.31(20), 2975-2977 (2006).
B. Potsaid, V. Jayaraman, J. G. Fujimoto, J. Jiang, P. J. Heim, and A. E. Cable, "MEMS tunable VCSEL light source for ultrahigh speed 60kHz-1MHz axial scan rate and long range centimeter class OCT imaging," in SPIE BiOS, (International Society for Optics and Photonics), (2012).
V. Jayaraman, G. D. Cole, M. Robertson, A. Uddin, and A. Cable, "High-sweep-rate 1310 nm MEMS-VCSEL with 150 nm continuous tuning range," Electron. Lett. 48(14), 867-869 (2012).
W. Wieser, W. Draxinger, T. Klein, S. Karpf, T. Pfeiffer, and R. Huber, "High definition live 3D-OCT in vivo: design and evaluation of a 4D OCT engine with 1 GVoxel/s," Biomed. Opt. Express 5(9), 2963-2977 (2014).
M.V. Sarunic, B.E. Applegate, and J.Izatt, "Real-Time Quadrature Projection Complex Conjugate Resolved Fourier Domain Optical Coherence Tomography," Optics Letters, vol. 31, No. 16, Aug. 15, 2006.
R. K. Wang, S. L. Jacques, Z. Ma, S. Hurst, S. R. Hanson, and A. Gruber, "Three dimensional optical angiography," Opt. Express 15(7), 4083-4097 (2007).
Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20(4), 4710-4725 (2012).
S. Makita, Y. Hong, M. Yamanari, T. Yatagai, and Y. Yasuno, "Optical coherence angiography," Opt. Express 14(17), 7821-7840 (2006).
S. Yazdanfar, M. Kulkarni, and J. Izatt, "High resolution imaging of in vivo cardiac dynamics using color Doppler optical coherence tomography," Opt. Express 1(13), 424-431 (1997).
B. Vakoc, S. Yun, J. de Boer, G. Tearney, and B. Bouma, "Phase-resolved optical frequency domain imaging," Opt. Express 13(14), 5483-5493 (2005).
M. R. Hee, E. A. Swanson, J. G. Fujimoto, and D. Huang, "Polarization-sensitive low-coherence reflectometer for birefringence characterization and ranging," J. Opt. Soc. Am. B 9(6), 903-908 (1992).
J. F. de Boer and T. E. Milner, "Review of polarization sensitive optical coherence tomography and Stokes vector determination," J. Biomed Opt. 7(3), 359-371 (2002).
M. Pircher, C. K. Hitzenberger, and U. Schmidt-Erfurth, "Polarization sensitive optical coherence tomography in the human eye," Prog. Retin. Eye. Res. 30(6), 431-451 (2011).
S. K. Nadkarni, M. C. Pierce, B. H. Park, J. F. de Boer, P. Whittaker, B. E. Bouma, J. E. Bressner, E. Halpern, S. L. Houser, and G. J. Tearney, "Measurement of Collagen and Smooth Muscle Cell Content in Atherosclerotic Plaques Using Polarization-Sensitive Optical Coherence Tomography," J. Am. Coll. Cardiol. 49(13), 1474-1481 (2007).
B. R. Biedermann, W. Wieser, C. M. Eigenwillig, T. Klein, and R. Huber, "Dispersion, coherence and noise of Fourier domain mode locked lasers," Opt. Express 17(12), 9947-9961 (2009).
M. Sarunic, M. A. Choma, C. Yang, and J. A. Izatt, "Instantaneous complex conjugate resolved spectral domain and swept-source OCT using 3×3 fiber couplers," Opt. Express 13(3), 957-967 (2005).
R. K. Wang, "In vivo full range complex Fourier domain optical coherence tomography," Appl. Phys. Lett. 90(5), 054103 (2007).
M. Yamanari, S. Makita, Y. Lim, and Y. Yasuno, "Full-range polarization-sensitive swept-source optical coherence tomography by simultaneous transversal and spectral modulation," Opt. Express 18(13), 13964-13980 (2010).
Amir Porat, Ori Katz, Esben Ravn Andresen, Herve Rigneault, Dan Oron, Sylvain Gigan, "Widefield Lensless Endoscopy via Speckle Correlations", Optics and Photonics News, Dec. 2016, p. 41.
Martin Ploschner, Tomas Tyc and Tomas Ciamar, "Seeing through chaos in multimode fibres", Nature Photonics, doi: 10:1038/NPHOTON.2015, Jul. 2015,112, pp. 529-538.
Tomas Cizmár and Kishan Dholakia, "Exploiting multimode waveguides for pure fibre-based imaging" Nature Communications, 3:1027, doi: 10.1038/ncomms2024, May 2012.
Martin Ploschner, Branislav Straka, Kishan Dholakia and Tomas Cizmar, "Fibre-based imaging: new challenges", Adaptive Optics and Wavefront Control for Biological Systems, Proc. of SPIE vol. 9335, 93350H, doi: 10.1117/12.2077693, Mar. 2015.
M. Ploschner, B. Straka, K. Dholakia, and T. Cizmar, "GPU accelerated toolbox for real-time beam-shaping in multimode fibres", Optics Express, 2014, vol. 22, No. 3, doi:10.1364/OE.22.002933.

(56) References Cited

OTHER PUBLICATIONS

Miguel A. Preciado, Michael Mazilu, Kishan Dholakia, "Multimode fibre correction for applications in optomechanics using a digital micromirror device", FTu1A.6, FiO/LS, OSA 2014.

Miguel A. Preciado, Kishan Dholakia, Michael Mazilu, "Real-time optical eigenmode characterization", FTh3G.5, FiO/LS, OSA 2014.

Reza Nasiri, Mahalati, Ruo, Yu Gu, and Joseph M. Kahn, "Resolution limits for imaging through multi-mode fiber", Optics Express, Jan. 2013, vol. 21, No. 1.

S. G. Adie, N. D. Shemonski, T. S. Ralston, P. S. Carney, S. A. Boppart, "Interferometric Synthetic Aperture Microscopy (ISAM)", In Optical Coherence Tomography: Technology and Applications. 2nd ed.; Drexler, W., Fujimoto, J. G., Eds.; Springer International Publishing, Switzerland, 2015, 965-1004, 2015.

Y. Xu, Y. Z. Liu, S. A. Boppart, P. S. Carney, "Automated Interferometric Synthetic Aperture Microscopy and Computational Adaptive Optics for Improved Optical Coherence Tomography", Applied Optics, 55, (8), 2034-2041, doi:10.1364/Ao.55.002034, 2016.

F. A. South, Y. Z. Liu, Y. Xu, N. D. Shemonski, P. S. Carney, S. A. Boppart, "Polarization-Sensitive Interferometric Synthetic Aperture Microscopy", Applied Physics Letters, 107, (21), DOI: Artn 211106 10.1063/1.4936236, 2015.

Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, vol. 4, No. 5, doi: 10.1364/OPTICA.4.000496, 2017.

Ruo Yu Gu, Reza Nasiri Mahalati, and Joseph M. Kahn, "Design of flexible multi-mode fiber endoscope", Optics Express, Oct. 2015,vol. 23, No. 21, doi:10.1364/OE.23.026905.

C. Bellanger, A. Brignon, J. Colineau, and J. P. Huignard, "Coherent fiber combining by digital holography", Optics Letters, Dec. 2008, vol. 33, No. 24.

Tomas Cizmar, "Exploiting multimode waveguides for in vivo imaging" SPIE Newsroom, http://www.spie.org/newsroom/6106-exploiting-multimode-waveguides-for-in-vivo-imaging, Sep. 2015.

Yuan-Zhi Liu, F. A. South, Y. Xu, P. S. Carney, and S. A. Boppart, "Computational optical coherence tomography", https://doi.org/10.1364/BOE.8.001549, Feb. 2017.

David B. Cole, Cheryl Sorace-Agaskar, Michele Moresco, Gerald Leake, Douglas Goolbaugh, and Michel R. Watts, "Integrated heterodyne interferometer with on-chip modulators and detectors", Optics Letters, vol. 40, No. 13, Jul. 1, 2015.

Chao Zuo, Jiasong Sun, Jiaji Li, Qian Chen, "Computational microscopy with programmable illumination and coded aperture", Proceedings of the SPIE, vol. 10250, doi: 10.1117/12.2266652, 2016.

Ioannis N. Papadopoulos, Salma Farahi, Christophe Moser, and Demetri Psaltis, "High-resolution, lensless endoscope based on digital scanning through a multimode optical fiber", Biomedical Optics Express, V. 4, No. 3. 2013.

Jason P. Moore and Matthew D. Rogge, "Shape sensing using multi-core fiber optic cable and parametric curve solutions", Optics Express, vol. 20, Issue 3, pp. 2967-2973, https://doi.org/10.1364/OE.20.002967, 2012.

Paul S. Westbrook, Tristan Kremp, Kenneth S. Feder, Wing Ko, Eric. M. Monberg, Hongchao Wu, Debra A. Simoff, Thierry F. Taunay, Roy. M. Ortiz , "Continuous multicore optical fiber grating arrays for distributed sensing applications", Journal of Lightwave Technology, v PP, Issue 99, pp. 1-5, doi:10.1109/JLT.2017.2661680, 2017.

Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, v 4, No. 5, https://doi.org/10.1364/OPTICA.4.000496, 2017.

J. Carpenter, B. J. Eggleton, and J. Schröder, "110×110 optical mode transfer matrix inversion", Opt. Express, vol. 22, pp. 96-101, 2014.

Joel Carpenter, "Everything you always wanted to know about Multimode Fiber", IEEE Photonics Society Newsletter, pp. 4-10, Aug. 2017.

Youngwoon Choi, Changhyeong Yoon Moonseok Kim Taeseok Daniel Yang Christopher Fang-Yen, Ramachandra R. Dasari, Kyoung Jin Lee, and Wonshik Choi, "Scanner-Free and Wide-Field Endoscopic Imaging by Using a Single Multimode Optical Fiber" Physical Review Letters, vol. 109, 203901, Nov. 2012.

Silvio Bianchi and Roberto Di Leonardo, "A multi-mode fiber probe for holographic micromanipulation and microscopy", Lab on a Chip, V. 121, 635, 2012.

T. S. Ralston, D. L. Marks, P. S. Carney, S. A. Boppart, "Interferometric synthetic aperture microscopy". Nature Physics, 3, (2), 129-134, 2007.

J. Carpenter, B. J. Eggleton, and J. Schröder, "Observation of Eisenbud-Wigner-Smith states as principal modes in multimode fibre," Nat Phot., vol. 9, No. 11, pp. 751-757, Nov. 2015.

J. Carpenter, B. J. Eggleton, and J. Schröder, "Comparison of principal modes and spatial eigenmodes in multimode optical fibre," Laser Photon. Rev., Dec. 2016.

J. Carpenter, B. J. Eggleton, and J. Schröder, "First demonstration of principal modes in a multimode fibre," in European Conference on Optical Communication, ECOC, 2014.

S. Fan and J. M. Kahn, "Principal modes in multimode waveguides," Opt. Lett, vol. 30, pp. 135-137, 2005.

J. Carpenter, B. J. Eggleton, and J. Schröder, "Complete spatiotemporal characterization and optical transfer matrix inversion of a 420 mode fiber," Opt. Lett., vol. 41, No. 23, pp. 5580-5583, 2016.

Bo Shuang, Wenxiao Wang, Hao She, Lawrence J. Tauzin, Charlotte Flateb, Jianbo Chen, Nicholas A. Moring, Logan D. C. Bishop, Kevin F. Kelly & Christy F. Landes, "Generalized recovery algorithm for 3D super-resolution microscopy using rotating point spread Functions", Scientific Reports, 6:30826, DOI: 10.1038/srep30826, 2016.

Ioannis N. Papadopoulos, Salma Farahi, Christophe Moser, and Demetri Psaltis, "Focusing and scanning light through a multimode optical fiber using digital phase conjugation", Optics Express, V. 20, No. 10, 2012.

A. M. Caravaca-Aguirre, E. Niv, and R. Piestun, "High-speed phase modulation for multimode fiber endoscope," Imaging Appl. Opt. (2014).

R. Y. Gu, R. N. Mahalati, and J. M. Kahn, "Noise-reduction algorithms for optimization-based imaging through multi-mode fiber," Opt. Express 22(12), 15118-15132 (2014).

D. Loterie, S. Farahi, I. Papadopoulos, A. Goy, D. Psaltis, and C. Moser, "Digital confocal microscopy through a multimode fiber," http://arxiv.org/abs/1502.04172 (2015).

E. E. Morales-Delgado, S. Farahi, I. N. Papadopoulos, D. Psaltis, and C. Moser, "Delivery of focused short pulses through a multimode fiber", Opt. Express 23(7), 9109-9120 (2015).

Y. Choi, C. Yoon, M. Kim, W. Choi, and W. Choi, "Optical imaging with the use of a scattering lens", IEEE J. Sel. Top. Quantum Electron. 20(2), 61-73 (2014).

S. Bianchi, V. P. Rajamanickam, L. Ferrara, E. Di Fabrizio, R. Di Leonardo, and C. Liberale, "High numerical aperture imaging by using multimode fibers with micro-fabricated optics", in CLEO: Science and Innovations (OSA, 2014), paper SM2N.6.

M. Plöschner and T. Čižmár, "Compact multimode fiber beam-shaping system based on GPU accelerated digital holography". Opt. Lett. 40(2), 197-200 (2015).

A. M. Caravaca Aguirre and R. Piestun, "Robustness of multimode fiber focusing through wavefront shaping", in Latin America Optics and Photonics Conference (2014).

S. Farahi, D. Ziegler, I. N. Papadopoulos, D. Psaltis, and C. Moser, "Dynamic bending compensation while focusing through a multimode fiber", Opt. Express 21(19), 22504 22514 (2013).

R. A. Panicker and J. M. Kahn, "Algorithms for compensation of multimode fiber dispersion using adaptive optics", J. Lightwave Technol. 27(24), 5790-5799 (2009).

R. A. Horn, Matrix Analysis, 2nd ed. (Cambridge University, 2013).

24. M. Sasaki, T. Ando, S. Nogawa, and K. Hane, "Direct photo-lithography on optical fiber end", Jpn. J. Appl. Phys. 41(Part 1, No. 6B), 4350-4355 (2002).

(56) References Cited

OTHER PUBLICATIONS

Antonio M. Caravaca-Aguirre, Eyal Niv, Donald B. Conkey, and Rafael Piestun, "Real-time resilient focusing through a bending multimode fiber", Optics Express, vol. 21, No. 10, DOI:10.1364/OE.21.012881, (2013).

Paul H. Beckwith, Ian McMichael, and Pochi Yeh, "Image distortion in multimode fibers and restoration by polarization-preserving phase conjugation", Optics Letters, vol. 12, No. 8, 1987.

D. Z. Anderson, M. A. Bolshtyansky and B. Ya. Zel'dovich, "Stabilization of the speckle pattern of a multimode fiber undergoing bending", Optics Letters, vol. 21, No. 11, Jun. 1996.

Ami Yaacobi, Jie Sun, Michele Moresco, Gerald Leake, Douglas Coolbaugh, and Michael R. Watt, "Integrated phased array for wide-angle beam steering", Opt. Lett. 39, 4575, doi: 10.1364/OL.39.004575, 2014.

Christopher V. Poulton, Matthew J. Byrd, Manan Raval, Zhan Su, Nanxi Li, Erman Timurdogan, Douglas Coolbaugh, Diedrik Vermeulen, and Michael R. Watts, "Large-scale silicon nitride nanophotonic phased arrays at infrared and visible wavelengths", Optics Letters, v. 42, No. 1, doi: 10.1364/OL.42.000021, 2017.

Christopher V. Poulton, Ami Yaccobi, Zhan Su, Matthew J. Byrd, and Michael R. Watts, "Optical Phased Array with Small Spot Size, High Steering Range and Grouped Cascaded Phase Shifters", Advanced Photonics 2016, OSA technical Digest, paper IW1B.2, doi: 10.1364/IPRSN.2016.IW1B.2, 2016.

Manan Raval, Ami Yaacobi, Daniel Coleman, Nicholas M. Fahrenkopf, Christopher Baiocco, Gerald Leake, Thomas N. Adam, Douglas Coolbaugh, and Michael R. Watts, "Nanophotonic Phased Array for Visible Light Image Projection", in IEEE Photonics Conference (2016), paper MG3.4, doi: 10.1109/IPCon.2016.7831042, 2016.

K. K. Mehta and R. J. Ram, "Precise and diffraction-limited waveguide-to-free-space focusing gratings," arXiv 1607.00107, 2016.

David Fattal, Zhen Peng, Tho Tran, Sonny Vo, Marco Fiorentino, Jim Brug & Raymond G. Beausoleil, "A multi-directional backlight for a wide-angle, glasses-free three-dimensional display", Nature 495, 348, 2013.

Martijn J. R. Heck, "Highly integrated optical phased arrays: photonic integrated circuits for optical beam shaping and beam steering", Nanophotonics, 6(1): 93-107, doi: 10.1515/nanoph-2015-0152, 2017.

Trevor K. Chan, Mischa Megens, Byung-Wook Yoo, John Wyras, Connie J. Chang-Hasnain, Ming C. Wu, and David A. Horsley, "Optical beamsteering using an 8×8 MEMS phased array with closed-loop interferometric phase control", Opt Express; 21:2807-15, 2013.

M. Raval, C. Poulton, and M. R. Watts, "Unidirection waveguide grating antennas with uniform emission for optical phased arrays", Optics Letters, v. 42, No. 12, doi: 10.1364/OL.42.002563, 2017.

A. Femius Koenderink, Andrea Alù, Albert Polman, "Nanophotonics: Shrinking light-based technology", Science, v. 348, No. 6234, doi: 10.1126/science.1261243, 2015.

Mikhail I. Shalaev, Jingbo Sun, Alexander Tsukernik, Apra Pandey, Kirill Nikolskiy, and Natalia M. Litchinitser, "High-Efficiency All-Dielectric Metasurfaces for Ultracompact Beam Manipulation in Transmission Mode", Nano Letters, 15(9), pp. 6261-6266, doi: 10.1021/acs.nanolett.5b02926, 2015.

Paul J. M. Suni, John Bowers, Larry Coldren, S.J. Ben Yoo, "Photonic Integrated Circuits for Coherent Lidar", 18th Coherent Laser Radar Conference, CLRC 2016, Jun. 26-Jul. 1, 2016.

Chao Li, Huijuan Zhang, Mingbin Yu, and G. Q. Lo, "CMOS-compatible High Efficiency Double-Etched Apodized Waveguide Grating Coupler", Opt. Expr., 21, pp. 7868, 2013.

Christopher Vincent Poulton, "Integrated LIDAR with Optical Phased Arrays in Silicon Photonics", MIT MS EECS Thesis, Sep. 2016.

S. J. Ben Yoo, Binbin Guan and Ryan P. Scott, "Heterogeneous 2D/3D Photonic Integrated Microsystems", Microsystems & Nanoengineering, v. 2, 16030; doi:10.1038/micronano.2016.30, 2016.

Francesco Aieta, Patrice Genevet, Nanfang Yu, Mikhail A. Kats, Zeno Gaburro, and Federico Capasso. "Out-of-Plane Reflection and Refraction of Light by Anisotropic Optical Antenna Metasurfaces with Phase Discontinuities", Nano Lett., 12 (3), pp. 1702-1706, doi: 10.1021/nl300204s, 2012.

Paul F. McManamon, Philip J. Bos, Michael J. Escuti, Jason Heikenfeld, Steve Serati, HuikaiXie, Edward A. Watson , "A Review of Phased Array Steering for Narrow-Band Electrooptical Systems", Proc. of the IEEE, 97, pp. 1078, doi: 10.1109/JPROC.2009.2017218, 2009.

Byung-Wook Yoo, Mischa Megens, Tianbo Sun, Weijian Yang, Connie J. Chang-Hasnain, David A. Horsley, and Ming C. Wu, "A 32×32 Optical Phased Array Using Polysilicon Sub-Wavelength High-Contrast-Grating Mirrors", Opt. Expr., 22, doi:10.1364/OE.22.019029, 2014.

Weihua Guo, Pietro R. A. Binetti, Chad Althouse , Milan L. Mašanović, Huub P. M. M. Ambrosius, Leif A. Johansson, Larry A. Coldren, "Two-Dimensional Optical Beam Steering with InP-based Photonic Integrated Circuits," IEEE J. Sel. Topics Quantum Electron., Special Issue on Semiconductor Lasers, 19, pp. 6100212, 2013.

J. C. Hulme, J. K. Doylend, M. J. R. Heck, J. D. Peters, M. L. Davenport, J. T. Bovington, L. A. Coldren, and J. E. Bowers, "Fully Integrated Hybrid Silicon Two Dimensional Beam Scanner", Optics Express, vol. 23, No. 5 doi:10.1364/OE.23.005861, p. 5861-5874; Feb. 25, 2015.

Brian W. Krause, Bruce G. Tiemann, and Philip Gatt, "Motion Compensated Frequency Modulated Continuous Wave 3D Coherent Imaging Ladar with Scannerless Architecture," Appl. Opt., 51, pp. 8745-8761 (2012).

Fei Ding, Zhuoxian Wang, Sailing He, Vladimir M. Shalaev, and Alexander V. Kildishev, "Broadband High-Efficiency Half-Wave Plate: A Supercell-Based Plasmonic Metasurface Approach", ACS Nano, doi: 10.1021/acsnano.5b00218, 2015.

Hooman Abediasl and Hossein Hashemi, "Monolithic optical phased-array transceiver in a standard SOI CMOS process", Opt. Express 23, 6509, doi: 10.1364/OE.23.006509, 2015.

David N. Hutchison, Jie Sun, Jonathan K. Doylend, Ranjeet Kumar, John Heck, Woosung Kim, Christopher T. Phare, Avi Feshali, and Haisheng Rong, "High-resolution aliasing-free optical beam steering", Optica 3, 887, doi: 10.1364/OPTICA.3.000887, 2016.

Firooz Aflatouni, Behrooz Abiri, Angad Rekhi, and Ali Hajimiri, "Nanophotonic coherent imager", Opt. Express 23, doi: 10.1364/OE.23.005117, 2015.

Tin Komljenovic, Roger Helkey, Larry Coldren, and John E. Bowers, "Sparse aperiodic arrays for optical beam forming and LIDAR", Opt. Express 25, 2511, doi: 10.1364/OE.25.002511, 2017.

Binbin Guan, Ryan P. Scott, Chuan Qin, Nicolas K. Fontaine, Tiehui Su, Carlo Ferrari, Mark Cappuzzo, Fred Klemens, Bob Keller, Mark Earnshaw, and S. J. B. Yoo, "Free-space coherent optical communication with orbital angular, momentum multiplexing/demultiplexing using a hybrid 3D photonic integrated circuit", Opt. Express 22, 145, doi: 10.1364/OE.22.000145, 2014.

William S. Rabinovich ; Peter G. Goetz; Marcel Pruessner ; Rita Mahon ;Mike S. Ferraro ; Doe Park ; Erin Fleet ; Michael J. DePrenger, "Free space optical communication link using a silicon photonic optical phased array", Proc. SPIE 9354, 93540B, doi:10.1117/12.2077222, 2015.

J. Sun, "Toward accurate and large-scale silicon photonics," MIT Ph.D. Thesis, 2013.

Drexler et al., Optical Coherence Tomography: Technology and Applications. 2nd ed. Springer International Publishing, Switzerland. 2015. Cover page and table of contents only, 9 pages.

Kerstin Worhoff, Rene M. De Ridder, B. Imran Akca, Markus Pollnau, "Silicon Oxynitride Technology for Integrated Optical Solutions in Biomedical Applications", In: 13th International Conference on Transparent Optical Networks 2011, Jun. 26-30, 2011, Stockholm, Sweden.

Dietrich, et al., In situ 3D Nanoprinting of Free-form Coupling Elements for Hybrid Photonic Integration, Nature Photonics, Apr. 2018, pp. 241-247, vol. 12, Macmillan Publishers Limited.

Muhammad Rodlin Billah, et al., Hybrid Integration of Silicon Photonics Circuits and InP Lasers by Photonic Wire Bonding, Jul. 2018, vol. 5, No. 7, pp. 876-883, Optica.

(56) References Cited

OTHER PUBLICATIONS

Dietrich, et al., In situ 3D Nanoprinting of Free-form Coupling Elements for Hybrid Photonic Integration, Nature Photonics, Apr. 2018, pp. 1-5, vol. 12, Macmillan Publishers Limited.
Trappen, et al. 3D-Printed Optics for Wafer-Scale Probing, 3 pages.
K. Takiguchi, et al., "Integrated-optic variable delay line and its application to a low-coherence reflectometer", Optics Letters, Oct. 15, 2005, pp. 2739-2741, vol. 30, No. 20, Optical Society of America.
Mahmoud S. Rasras, et al., "Integrated resonance-enhanced variable optical delay lines", IEEE Photonics Technology Letters, Apr. 4, 2005, pp. 834-836, vol. 17, No. 4.
Leimeng Zhuang, et al., "Low-loss, high-index-contrast Si3N4/SiO2 optical waveguides for optical delay lines in microwave photonics signal processing", Optics Express, Oct. 17, 2011, pp. 23162-23170, vol. 19, No. 23.
J.P. Mack, et al., "Photonic Integrated Circuit Switch Matrix and Waveguide Delay Lines for Optical Packet Synchronization" ECOC 2008, Sep. 21-25, 2008, pp. 87-88, vol. 4, IEEE, Brussels, Belgium.
Jingya Xie, et al., "Seven-bit reconfigurable optical true time delay line based on silicon integration", Optics Express, Sep. 22, 2014, pp. 22707-22715 vol. 22, No. 19.
Hansuek Lee et al., "Ultra-low-loss optical delay line on a silicon chip", Nature Communications, May 2012, 7 pages.
Xiaolong Wang, et al., "Phase error corrected 4-bit true time delay module using a cascaded 2×2 polymer waveguide switch array" Applied Optics, Jan. 20, 2007, pp. 379-383 vol. 46, No. 3.
Maciej Wojtkowski, et al., "Ultrahigh-resolution, high-speed, Fourier domain optical coherence tomography and methods for dispersion compensation", Optics Express, May 31, 2004, pp. 2404-2422, vol. 12, No. 11.
Dierck Hillmann et al., "Common approach for compensation of axial motion artifacts in swept-source OCT and dispersion in Fourier-domain OCT", Optics Express, Mar. 12, 2012, pp. 6761-6676, vol. 20, No. 6.
Norman Lippok, et al., "Dispersion compensation in Fourier domain optical coherence tomography using the fractional Fourier transform", Optics Express, Oct. 8, 2012, pp. 23398-23413, vol. 20, No. 1.
Kaname Jinguji, et al., "Two-port optical wavelength circuits composed of cascaded Mach-Zehnder interferometers with point-symmetrical configurations", Journal of Lightwave Technology, Oct. 10, 1996, pp. 2301-2310, vol. 14, No. 10.
Xingchen Ji, et al., "On-chip tunable photonic delay line", APL Photonics, 2019, pp. 090803-1-090803-7, 4doi 10.1063/1.5111164.
EunSeo Choi, et al., "All-fiber variable optical delay line for applications in optical coherence tomography: feasibility study for a novel delay line", Optics Express, Feb. 21, 2005, pp. 1334-1345, vol. 13, No. 4.
Hailong Zhou, et al., "All-in-one silicon photonic polarization processor", Nanophotonics, 2019, pp. 2257-2267, vol. 8, No. 12.
Fred Heismann, "Analysis of a Reset-Free Polarization Controller for Fast Automatic PolarizationStabilization in Fiber-optic Transmission Systems", Journal of Lightwave Technology, Apr. 1994, pp. 690-699, vol. 12, No. 4.
Reinhold Noe, et al., "Automatic endless polarization control with integrated-optical Ti:LiNbO3 polarization transformers", Reinhold Noe, Optics Letters, Jun. 1988, pp. 527-529, vol. 13, No. 6.
Tao Chu, et al., "Compact 1 Å~N thermo-optic switches based on silicon photonic wire waveguides", Optics Express, Dec. 12, 2005, pp. 10109-10114, vol. 13, No. 25.
Xiaoxi Wang, et al., "Compact high-extinction-ratio silicon photonic variable optical attenuators (VOAs)", Proceedings of the Conference on Lasers and Electro Optics (CLEO), 2 pages, Paper SW1N.7, 2017.
Reinhold Noe,et al., "Endless Polarization Control Systems for Coherent Optics", Journal of Lightwave Technology, Jul. 1988, pp. 1199-1208, vol. 6, No. 7.

Ansheng Liu, et al., "High-speed optical modulation based on carrier depletion in a silicon waveguide", Optics Express, Jan. 22, 2007, pp. 660-668, vol. 15, No. 2.
Niels Quack, et al., "MEMS-Enabled Silicon Photonic Integrated Devices and Circuits", IEEE Journal of Quantum Electronics, Feb. 2020, vol. 56, No. 1.
Christopher R. Doerr, et al., "Monolithic PDM-DQPSK receiver in silicon", 36th European Conference and Exhibition on Optical Communication 2010 3 pages.
Benjamin G. Lee, et al., "Silicon Photonic Switch Fabrics: Technology and Architecture", Journal of Lightwave Technology, DOI 10.1109/JLT.2018.2876828, 2018, 15 pages.
Xin Tu, et al., "State of the Art and Perspectives on Silicon Photonic Switches", Micromachines, 2019, 19 pages, vol. 10, No. 55, doi:10.3390/mi10010051.
Richard Soref, "Tutorial: Integrated-photonic switching structures", APL Photonics, Jan. 29, 2018, 19 pages, doi.org/10.1063/1.5017968.
Benjamin Koch, et al., "Versatile endless optical polarization controller/tracker/demultiplexer", Optics Express, Apr. 7, 2014, pp. 8259-8276, vol. 22, No. 7.
P. Velha, et al., "Wide-band polarization controller for Si photonic integrated circuits", Optics Letters, Dec. 15, 2016, pp. 5656-5659, vol. 41, No. 21.
Luis A. Bru, et al., "Integrated optical frequency domain reflectometry device for characterization of complex integrated devices", Optics Express, Nov. 12, 2018, vol. 26, No. 23, doi:10.1364/OE.26.030000.
U.S. Appl. No. 15/147,775, filed Dec. 8, 2016, USPTO.
C. Boudoux, et al., Rapid wavelength-swept spectrally encoded confocal microscopy, Optics Express, Oct. 3, 2005, pp. 8214-8221, vol. 13, No. 20, OSA.
Dongyao Cui, et al., Multifiber angular compounding optical coherence tomography for speckle reduction, Optics Letter, Jan. 1, 2017, pp. 125-128, vol. 42, No. 1, Optical Society of America.
Daniel J. Fechtig, et al., Line-field parallel swept source MHz OCT for structural and functional retinal imaging, Biomedical Optics Express, Mar. 1, 2015, pp. 716-735, vol. 6, No. 3, OSA.
Simon Lemire-Renaud, et al., Double-clad fiber coupler for endoscopy, Optics Express, May 10, 2020, 9755-9764, vol. 18, No. 10, OSA.
Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.
Seen Young Ryu, et al., Combined system of optical coherence tomography and fluorescence spectroscopy based on double-cladding fiber, Optics Letters, pp. 2347-2349, Oct. 15, 2008, vol. 33, No. 20.
Juan Sancho-Dura, et al., Handheld multi-modal imaging for point-of-care skin diagnosis based on akinetic integrated optics optical coherence tomography, Biophotonics Journal, 2018, pp. 1-6, 2018, Wiley-VCH Verlag, GmbH & Co. KGaA Weinheim.
Tuqiang Xie, et al., Fiber-optic-bundle-based optical coherence tomography, Optics Letters, Jul. 15, 2005, pp. 1803-1805, vol. 30, No. 14.
Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.
Chao Zhou, et al., Space-division multiplexing optical coherence tomography, Optics Express, Aug. 12, 2013, pp. 19219-19227, vol. 21, No. 16, OSA.
G. Roelkens, D. Vermeulen, S. Selvaraja, Student Member, IEEE, R. Halir, W. Bogaerts, Member, IEEE, and D. Van Thourhout, "Grating-Based Optical Fiber Interfaces for Silicon-on-Insulator Photonic Integrated Circuits", IEEE Journal of Selected Topics in Quantum Electronics, vol. 17, No. 3, May/Jun. 2011.
Attila Mekis, Steffen Gloeckner, Gianlorenzo Masini, Adithyaram Narasimha, Member, IEEE, Thierry Pinguet, Subal Sahni, and Peter De Dobbelaere,"A Grating-Coupler-Enabled CMOS Photonics Platform". IEEE Journal of Selected Topics in Quantum Electronics, vol. 17, Issue 3, May/Jun. 2011.

(56) References Cited

OTHER PUBLICATIONS

Neil Na, Harel Frish, I-Wei Hsieh, Oshrit Harel, Roshan George, Assia Barkai, and Haisheng Rong, "Efficient broadband silicon-on-insulator grating coupler with low backreflection", Optics Letters, vol. 36, No. 11, Jun. 1, 2011.

Wissem Sfar Zaoui, María Félix Rosa, Wolfgang Vogel, Manfred Berroth Jörg Butschke, and Florian Letzkus, "Cost-effective CMOS-compatible grating couplers with backside metal mirror and 69% coupling efficiency", Optics Express, vol. 20, No. 26, Dec. 10, 2012.

Vilson R. Almeida, Roberto R. Panepucci, and Michal Lipson, "Nanotaper for compact mode conversion", Optics Letters, vol. 28, No. 15, Aug. 1, 2003.

Anatol Khilo, Miloš A. Popović, Mohammad Araghchini, and Franz X. Kärtner, "Efficient planar fiber-to-chip coupler based on two-stage adiabatic evolution", Optics Express, vol. 18, No. 15, Jul. 19, 2010.

Long Chen, Christopher R. Doerr, Young-Kai Chen, and Tsung-Yang Liow, "Low-Loss and Broadband Cantilever Couplers Between Standard Cleaved Fibers and High-Index-Contrast Si3N4 or Si Waveguides", IEEE Photonics Technology Letters, vol. 22, No. 23, Dec. 1, 2010.

Alan Y. Liu, Chong Zhang, Justin Norman, Andrew Snyder, Dmitri Lubyshev, Joel M. Fastenau, Amy W. K. Liu, Arthur C. Gossard, and John E. Bowers, "High performance continuous wave 1.3 lm quantum dot lasers on silicon", Applied Physics Letters, 104, 041104 (2014).

Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.

Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.

C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas", Optics Express, vol. 21, No. 4, Feb. 25, 2013.

Jie Sun, Erman Timurdogan, Ami Yaacobi, Ehsan Shah Hosseini, and Michel R. Watts, "Large-scale nanophotonic phased array", Nature, vol. 493, Jan. 10, 2013.

Ami Yaacobi Erman Timurdogan, and Michael R. Watts, "Vertical emitting aperture nanoantennas", Optics Letters, vol. 37, No. 9, May 1, 2012.

J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.

Karel Van Acoleyen, Hendrick Rogier, and Roel Baets, "Two-dimensional optical phased array antenna on silicon-on-insulator", Optics Express, vol. 18, No. 13, Jun. 21, 2010.

James A. Burns, Brian F. Aull, Chenson K. Chen, Chang-Lee Chen, Craig L. Keast, Jeffrey M. Knecht, Vyshanavi Suntharalingam, Keith Warner, Peter W. Wyatt, and Donna-Ruth W. Yost, "A Wafer-Scale 3-D Circuit Integration Technology", IEEE Transactions on Electronic Devices, vol. 53, No. 10, Oct. 2006.

Dirk Lorenser, C. Christian Singe, Andrea Curatolo, and David D. Sampson, "Energy-efficient low-Fresnel-number Bessel beams and their application in optical coherence tomography", Optics Letters, vol. 39, No. 3, Feb. 1, 2014.

Niklas Weber, Dominik Spether, Andreas Seifert, and Hans Zappe, "Highly compact imaging using Bessel beams generated by ultraminiaturized multi-micro-axicon systems", Journal of Optical Society of America A. vol. 29, No. 5, May 2012.

Z. Xie, B. Armbruster, and T. Grosjean, "Axicon on a gradient index lens (AXIGRIN): integrated otial bench for Bessel beam generation from a point-like source", Applied Optics, vol. 53, Issue 26, (2014).

G.S. Sokolovskii, V.V. Dudelev, S.N. Losev, K.K. Soboleva, A.G. Deryagin, K.A. Fedorovac, V.I. Kuchinskii, W. Sibbett, E.U. Rafailov, "Bessel beams from semiconductor light sources", Progress in Quantum Electronics, vol. 38, No. 4, Jul. 2014.

F. Merola ; S. Coppola ; V. Vespini ; S. Grilli ; P. Ferraro ; D. Balduzzi ; A. Galli ; R. Puglisi, "Fabrication and test of polymeric microaxicons", Proceedings of the SPIE, doi:10.1117/12.922572, Jun. 1, 1012.

Paul Steinvurzel, Khwanchai Tantiwanichapan, Masao Goto, and Siddharth Ramachandran, "Fiber-based Bessel beams with controllable diffraction-resistant distance", Optics Letters, vol. 36, No. 23, 2011.

Cedric Blatter ; Branislav Grajciar ; Christoph M. Eigenwillig; Wolfgang Wieser; Benjamin R. Biedermann; Robert Huber; Rainer A. Leitgeb, "High-speed functional OCT with self-reconstructive Bessel illumination at 1300 nm", Proceedings of the SPIE, doi:10.1117/12.889669, Jun. 1, 2011.

James G. Fujimoto, Eric Swanson, Robert Huber, European Inventor Award 2017, Jun. 15, 2017, 3 pages. PRWeb.

Manon Rostykus, and Christophe Moser, "Compact lensless off-axis transmission digital holographic microscope," Opt Ex. 25(14), 16652-16659 (2017).

Damien Loterie, Demetri Psaltis, and Christophe Moser, "Bend translation in multimode fiber imaging," Opt. Ex. 25(6), 6263-6273 (2017).

Edgar E. Morales-Delgado, Demetri Psaltis, and Christophe Moser, "Two-photon imaging through a multimode fiber," Opt. Ex. 23(25), 32158-32170 (2015).

Damien Loterie, Sebstianus A. Goorden, Demetrie Psaltis, and Christophe Moser, "Confocal microscopy through a multimode fiber using optical correlation," Opt. Lett. 40(24), 5754-5757 (2015).

Siddharth Sivankutty, Esben Ravn Andresen, Rosa Cossart, Geraud Bouwmans, Serge Monneret, and Herve Rigneault, Ultra-thin rigid endoscope: two-photon imaging through a graded-index, 2015.

Sean C. Warren, Youngchan Kim, James M. Stone, Claire Mitchell, Jonathan C. Knight, Mark A. A. Neil, Carl Paterson, Paul M. W. French, and Chris Dunsby, "Adaptive multiphoton endomicroscopy through a dynamically deformed multicore optical fiber using proximal detection," Opt. Ex. 24(19), 21474-21484 (2016).

Alexander Fertman and Dvir Yelin, "Image transmission through an optical fiber using real-time modal phase restoration," JOSAB 30(1), 149-157 (2013).

Mickael Mounaix, Hilton B. de Aguiar, and Sylvain Gigan, "Temporal recompression through a scattering medium via a broadband transmission matrix," ArXiv (2017).

S. M. Popoff, G. Lerosey, R. Carminati, M. Fink, A.C. Boccara, and S. Gigan, "Measuring the Transmission Matrix in Optics : An Approach to the Study and Control of Light Propagation in Disordered Media," Phys. Rev. Lett. 104(10), 100601-100605 (2010).

Jürgen W. Czarske, Daniel Haufe, Nektarios Koukourakis, and Lars Büttner, "Transmission of independent signals through a multimode fiber using digital optical phase conjugation," Opt. Ex. 24(13), 15128-15136 (2016).

J. M. Stone, H. A. C. Wood, K. Harrinton, and T. A. Birks, "Low index contrast imaging fibers," Opt. Lett. 42(8), 1484-1487 (2017).

Harry A. C. Wood, Kerrianne Harrington, James M. Stone, Tim A. Birks, and Jonathan C. Knight, "Quantitative characterization of endoscopic imaging fibers," Opt. Ex. 25(3), 1985-1992 (2017).

Antonio M. Caravaca-Aguirre and Rafael Piestun, "Single multimode fiber endoscope," Opt Ex. 25(3), 1656-1665 (2017).

Ivan Gusachenko, Mingahou Chen, and Kishan Dholakia, "Raman imaging through a single multimode fibre," Opt. Ex. 25(12), 13782-13798 (2017).

Tomas Cizmar, and Kishan Dholakia, "Shaping the light transmission through a multimode optical fibre: complex transformation analysis and applications in biophotonics," Opt. Ex. 19(20), 18871-8884 (2011).

Moussa N'Gom, Theodore B. Norris, Eric Michielssen, Raj Rao Nadakuditi, "Mode Control in a Multimode Fiber Through Acquiring its Transmission Matrix from a Reference-less Optical System," ArXiv (2017).

Roberto Di Leonardo and Silvio Bianchi, "Hologram transmission through multi-mode optical fibers," Opt. Ex. 19(1), 247-254 (2011).

(56) References Cited

OTHER PUBLICATIONS

Carmelo Rosales-Guzman, Nkosiphile Bhebhe, Nyiku Mahonisi, and Andrew Forbes, "Multiplexing 200 modes on a single digital hologram," ArXiv (2017).
Peng Lu, Matthew Shipton, Anbo Wang, Shay Soker, and Yong Xu, "Adaptive control of waveguide modes in a two-mode fiber," Opt. Ex. 22(3), 2955-2964 (2014).
Shamir Rosen, Doron Gilboa, Ori Katz, Yaron Silberberg, "Focusing and Scanning through Flexible Multimode Fibers without Access to the Distal End", 8 pages, 2015.
Pablo Eugui, Antonia Lichtenegger, Marco Augustin, Danielle J. Harper, Martina Muck, Thomas Roetzer, Andreas Wartak, Thomas Konegger, Georg Widhalm, Christoph K. Hitzenberger, Adelheid Woehrer, and Bernhard Baumann, Beyond backscattering: Optical neuroimaging by BRAD, arXiv:1712.00361v1 [physics.optics] Dec. 1, 2017.
Carmelo Rosales-Guzmán and Andrew Forbes, "How to Shape Light with Spatial Light Modulators", SPIE Spotlight, doi: http://dx.doi.org/10.1117/3.2281295, 2017.
Lucas B. Soldano and Erik C. M. Pennings, "Optical Multi-Mode Interference Devices Based on Self-Imaging: Principles and Applications", Journal of Lightwave Technology, vol. 13, No. 4, Apr. 1995.
Victor Arrizón, Ulises Ruiz, Rosibel Carrada, and Luis A. González, "Pixelated phase computer holograms for the accurate encoding of scalar complex fields", J. Opt. Soc. Am. A/vol. 24, No. 11/Nov. 2007.
Jeff Demas, Lars Rishøj, and Siddharth Ramachandran*, Free-space beam shaping for precise control and conversion of modes in optical fiber,vol. 23, No. 22 DOI:10.1364/OE.23.028531, 2015.
S. M. Popoff, G. Lerosey, R. Carminati, M. Fink, A.C. Boccara, S. Gigan , "Measuring the Transmission Matrix in Optics: An Approach to the Study and Control of Light Propagation in Disordered Media", arXiv:0910.5436v2 [physics.optics] Jan. 18, 2010.
Kaicheng Liang, et al., "Cycloid Scanning for Wide Field Optical Coherence Tomography Endomicroscopy and Angiography in Vivo", Optica, Jan. 2018, pp. 36-43, vol. 5, No. 1.
Meena Siddiqui, et al., "High-Speed Optical Coherence Tomography by Circular Interferometric Ranging", Nature Photonics, Feb. 2018, pp. 111-116, vol. 12, Macmillan Publishers, 2018.
B. Imran AKCA, "Non-Moving Scanner Design for OCT Systems", Optics Express, Dec. 12, 2016, pp. 28459-28466, vol. 24, No. 25, Optical Society of America.
U.S. Appl. No. 16/864,056, filed Apr. 30, 2020, USPTO.
S. Yun, G. Tearney, J. de Boer, and B. E. Bouma, "Removing the depth-degeneracy in optical frequency domain imaging with frequency shifting," Opt. Express 12(20), 4822-4828 (2004).
B. J. Vakoc, S. H. Yun, G. J. Tearney, and B. E. Bouma, "Elimination of depth degeneracy in optical frequency-domain imaging through polarization-based optical demodulation," Opt. Lett. 31(3), 362-364 (2006).
M. Siddiqui, S. Tozburun, E. Z. Zhang, and B. J. Vakoc, "Compensation of spectral and RF errors in swept-source OCT for high extinction complex demodulation," Opt. Express 23, 5508-5520 (2015).
K.-S. Lee, P. Meemon, W. Dallas, K. Hsu, and J. P. Rolland, "Dual detection full range frequency domain optical coherence tomography," Opt. Lett. 35(7), 1058-1060 (2010).
B. Hofer, B. Považay, B. Hermann, A. Unterhuber, G. Matz, and W. Drexler, "Dispersion encoded full range frequency domain optical coherence tomography," Opt. Express 17(1), 7-24 (2009).
T.-H. Tsai, B. Potsaid, Y. K. Tao, V. Jayaraman, J. Jiang, P. J. S. Heim, M. F. Kraus, C. Zhou, J. Hornegger, H. Mashimo, A. E. Cable, and J. G. Fujimoto, "Ultrahigh speed endoscopic optical coherence tomography using micromotor imaging catheter and VCSEL technology," Biomed. Opt. Express 4(7), 1119-1132 (2013).
B. Baumann, W. Choi, B. Potsaid, D. Huang, J. S. Duker, and J. G. Fujimoto, "Swept source Fourier domain polarization sensitive optical coherence tomography with a passive polarization delay unit," Opt. Express 20(9), 10229-10241 (2012).
Z. Wang, H.-C. Lee, O. O. Ahsen, B. Lee, W. Choi, B. Potsaid, J. Liu, V. Jayaraman, A. Cable, M. F. Kraus, K. Liang, J. Hornegger, and J. G. Fujimoto, "Depth-encoded all-fiber swept source polarization sensitive OCT," Biomed. Opt. Express 5(9), 2931-2949 (2014).
B. H. Park, M. C. Pierce, B. Cense, and J. F. de Boer, "Jones matrix analysis for a polarization-sensitive optical coherencetomography system using fiber-optic components," Opt. Lett. 29(21), 2512-2514 (2004).
H. Pahlevaninezhad, A. Lee, L. Cahill, S. Lam, C. MacAulay, and P. Lane, "Fiber-Based Polarization Diversity Detection for Polarization-Sensitive Optical Coherence Tomography," Photonics 1(4), 283-295 (2014).
T. S. Ralston, D. L. Marks, P. S. Carney, and S. A. Boppart, "Interferometric synthetic aperture microscopy," Nat. Phys. 3(2), 129-134 (2007).
U. Morgner, W. Drexler, F. Kärtner, X. Li, C. Pitris, E. Ippen, and J. G. Fujimoto, "Spectroscopic optical coherence tomography," Opt. Lett. 25(2), 111-113 (2000).
R. Huber, M. Wojtkowski, J. G. Fujimoto, J. Y. Jiang, and A. E. Cable, "Three-dimensional and C-mode OCT imaging with a compact, frequency swept laser source at 1300 nm," Optics Express 13(26), 10523-10538 (2005).
R. Huber, M. Wojtkowski, K. Taira, J. G. Fujimoto, and K. Hsu, "Amplified, frequency swept lasers for frequency domain reflectometry and OCT imaging: design and scaling principles," Optics Express 13(9), 3513-3528 (2005).
B. Potsaid, I. Gorczynska, V. J. Srinivasan, Y. L. Chen, J. Jiang, A. Cable, and J. G. Fujimoto, "Ultrahigh speed spectral / Fourier domain OCT ophthalmic imaging at 70,000 to 312,500 axial scans per second," Optics Express 16(19), 15149-15169 (2008).
Marinko V. Sarunic, Brian E. Applegate, and Joseph A. Izatt, "Real-time quadrature projection complex conjugate resolved Fourier domain optical coherence Tomography", Optics Letters, vol. 31, No. 16, Aug. 15, 2006.
Jiefeng Xi, Li Huo, Jiasong Li and Xingde Li, "Generic real-time uniform K-space sampling method for high-speed swept-Source optical coherence tomography", Optics Express, vol. 18, No. 9, Apr. 26, 2010.
V. Jayaraman, G.D. Cole, M. Robertson, C. Burgner, D. John, A. Uddin and A. Cable, "Rapidly swept, ultra-widely-tunable 1060 nm MEMS-VCSELs", Electronics Letters, Oct. 11, 2012 vol. 48 No. 21.
G. J. Tearney, R. H. Webb, and B. E. Bouma, "Spectrally Encoded Confocal Microscopy", Optics Letters, vol. 23, No. 15, Aug. 1, 1998.
Chen D. Lu, Martin F. Kraus, Benjamin Potsaid, Jonathan J. Liu, WooJhon Choi, Vijaysekhar Jayaraman, Alex E. Cable, Joachim Hornegger, Jay S. Duker and James G. Fujimoto, "Handheld ultrahigh speed swept source optical coherence tomography instrument using a MEMs scanning mirror", Biomedical Optics Express, vol. 5, No. 1, Jan. 1, 2014.
V. D. Nguyen, N. Weiss, W. Beeker, M. Hoekman, A. Leinse, R. G. Heideman, T. G. van Leeuwen, and J. Kalkman, "Integrated-optics-based swept-source optical coherence tomography," Opt. Lett. 37(23), 4820-4822 (2012).
B. I. Akca, V. Nguyen, J. Kalkman, N. Ismail, G. Sengo, S. Fei, A. Driessen, T. G. van Leeuwen, M. Pollnau, K. Worhoff, and R. M. de Ridder, "Toward Spectral-Domain Optical Coherence Tomography on a Chip," IEEE J. Sel. Top. Quantum Electron. 18(3), 1223-1233 (2012).
V. D. Nguyen, B. I. Akca, K. Wörhoff, R. M. De Ridder, M. Pollnau, T. G. van Leeuwen, and J. Kalkman, "Spectral domain optical coherence tomography imaging with an integrated optics spectrometer," Opt. Lett. 36, 1293-1295 (2011).
G. Yurtsever, B. Považay, A. Alex, B. Zabihian, W. Drexler, and R. Baets, "Photonic integrated Mach-Zehnder interferometer with an on-chip reference arm for optical coherence tomography," Biomed. Opt. Express 5(4), 1050-1061 (2014).
G. Yurtsever, N. Weiss, J. Kalkman, T. G. van Leeuwen, and R. Baets, "Ultra-compact silicon photonic integrated interferometer for swept-source optical coherence tomography," Opt. Lett. 39(17), 5228-5231 (2014).

(56) References Cited

OTHER PUBLICATIONS

B. I. Akca, B. Povazay, A. Alex, K. Worhoff, R. M. de Ridder, W. Drexler, and M. Pallnau, "Miniature spectrometer and beam splitter for an optical coherence tomography on a silicon chip", Optics Express, vol. 31, No. 14, Jul. 3, 2014.

Kyle Preston, Arthur Nitkowski, Nicolás Sherwood-Droz, Andrew Berkeley, Bradley S. Schmid, and Arsen R. Hajian, OCTANE: Optical Coherence Tomography Advanced Nanophotonic Engine, CLEO 2013 Technical Digest, Paper AW3I.5, Jun. 9-14, 2013.

Daniel Neill, Luke Stewart, Huiping Li, Tom Killin, Fan Chen, Steve Frisken, Glenn Baxter, Simon Poole, "Compact polarization diverse receiver for biomedical imaging Applications", SPIE Proceedings, vol. 7891, Jan. 22, 2011.

Arthur Nitkowski, Kyle Preston, Nicolás Sherwood-Droz, Andrew Berkeley, Bradford B. Behr, Bradley S. Schmidt, and Arsen R. Hajian, "Nano Spectrometer for Optical Coherence Tomography", Imaging and Applied Optics Conference, Paper AM1B.3, (2013).

B. Imran Akca, "Spectral-Domain Optical Coherence Tomography on a Silicon Chip", PhD Thesis. University of Twente, (2012).

D. Culemann, A. Knuettel, and E. Voges, "Integrated optical sensor in glass for optical coherence tomography," IEEE J. Sel. Topics Quantum Electron., vol. 6, No. 5, pp. 730-734, Oct. 2000.

E. Margallo-Balbas, M. Geljon, G. Pandraud, and P. J. French, "Miniature 10 kHz thermo-optic delay line in silicon," Opt. Lett., vol. 35, No. 23, pp. 4027-4029, Dec. 2010.

B. Imran Akca, Markus Pollnau, Kerstin Worhoff, Rene M. De Ridder, "Silicon Oxynitride Technology for Integrated Optical Solutions in Biomedical Applications", In: 13th International Conference on Transparent Optical Networks 2011, Jun. 26-30, 2011, Stockholm, Sweden.

G. Yurtsever, P. Dumon, W. Bogaerts, and R. Baets, "Integrated photonic circuit in silicon on insulator for Fourier domain optical coherence tomography," in Proc. SPIE, Opt. Coherence Tomography Coherence Domain Opt. Methods Biomed. XIV, vol. 7554, San Francisco, CA, 2010, pp. 1-5, 2010.

V. D. Nguyen, N. Ismail, F. Sun, K. Wörhoff, T. G. van Leeuwen, and J. Kalkman, "SiON integrated optics elliptic couplers for Fizeau-based optical coherence tomography," IEEE J. Lightw. Technol., vol. 28, No. 19, pp. 2836-2842, Sep. 2010.

Haitham Omran, Yasser M. Sabry, Mohamed Sadek, Khaled Hassan, Mohamed Y. Shalaby and Diaa Khalil, "Deeply-Etched Optical MEMS Tunable Filter for Swept Laser Source Applications", IEEE Photonics Technology Letters. vol. 26, No. 1, Jan. 2014.

Firooz Aflatouni, Behrooz Abiri, Angad Rekhi, and Ali Hajimiri, "Nanophotonic coherent imager", Optics Express, vol. 23, No. 4, doi: 10.1364/OE.23.005117, 2015.

Gyeong Cheol Park, Weiqi Xue, Elizaveta Semenova, Kresten Yvind, Jesper Mørk, and Il-Sug Chung, "III-V/SOI Vertical Cavity Laser with In-plane Output into a Si Waveguide", Paper W2A.17, Proceedings of the Optical Fiber Communication Conference, 2015.

K. Worhoff, C. G. H. Roeloffzen, R. M. de Ridder, A. Driessen, and P. V. Lambeck, "Design and application of compact and highly tolerant polarization-independent waveguides," IEEE J. Lightw. Technol., vol. 25, No. 5, pp. 1276-1282, May 2007.

S. K. Selvaraja, W. Bogaerts, P. Absil, D. Van Thourhout, and R. Baets, "Record low-loss hybrid rib/wire waveguides for silicon photonic circuits," Group IV Photonics (2010).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon-on-insulator platform," Opt. Express 18(17), 18278-18283 (2010).

D. Vermeulen, S. Selvaraja, P. Verheyen, P. Absil, W. Bogaerts, D. Van Thourhout, and G. Roelkens, "Silicon-on-insulator polarization rotator based on a symmetry breaking silicon overlay," IEEE Photonics Technol. Lett. 24(5), 482 (2012).

A. Mekis, A. Dodabalapur, R. Slusher, and J. D. Joannopoulos, "Two-dimensional photonic crystal couplers for unidirectional light output," Opt. Lett. 25(13), 942-944 (2000).

L. Chen, C. R. Doerr, L. Buhl, Y. Baeyens, and R. A. Aroca, "Monolithically integrated 40-wavelength demultiplexer and photodetector array on silicon," IEEE Photonics Technol. Lett. 23(13), 869-871 (2011).

C. R. Doerr, L. Chen, D. Vermeulen, T. Nielsen, S. Azemati, S. Stulz, G. McBrien, X.-M. Xu, B. Mikkelsen, M. Givehchi, C. Rasmussen, and S. Y. Park, "Single-chip silicon photonics 100-GB/s coherent transceiver," in Optical Fiber Communication Conference, (Optical Society of America, 2014), Th5C. 1.

M. Izutsu, S. Shikama, and T. Sueta, "Integrated optical SSB modulator/frequency shifter," IEEE J. Quant. Electron., vol. 2, No. 11, pp. 2225-2227, 1981.

D. Taillert, H. Chong, P. I. Borel, L. H. Frandsen, R. M. D. L. Rue, and R. Baets, "A compact two-dimensional grating coupler used as a polarization splitter", IEEE Photon. Tech. Lett., vol. 15, pp. 1249-1251, 2003.

R. Nagarajan and Others, "10 Channel, 100Gbit/s per Channel, Dual Polarization, Coherent QPSK, Monolithic InP Receiver Photonic Integrated Circuit", Optical Fiber Communication Conference Proceedings, p. OML7, 2011.

N. Dupuis, C. R. Doerr, L. Zhang, L. Chen, N. J. Sauer, P. Dong, L. L. Buhl, and D. Ahn, "InP-based comb generator for optical OFDM," J. Lightw. Technol., 2011.

S. Chandrasekhar and Xiang Liu, "Enabling Components for Future High-Speed Coherent Communication Systems", Optical Fiber Communication Conference Tutorial, 2011.

\* cited by examiner

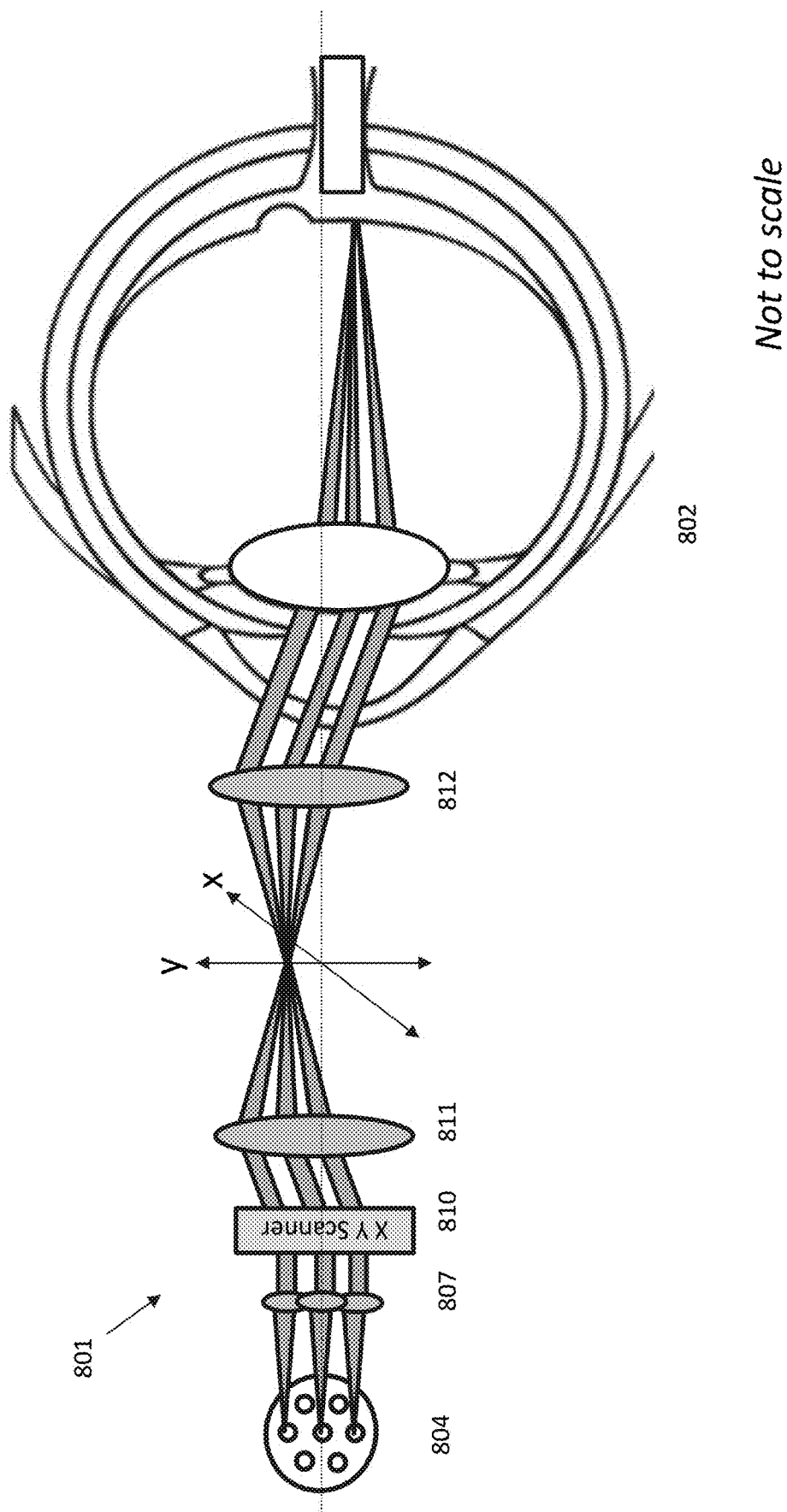

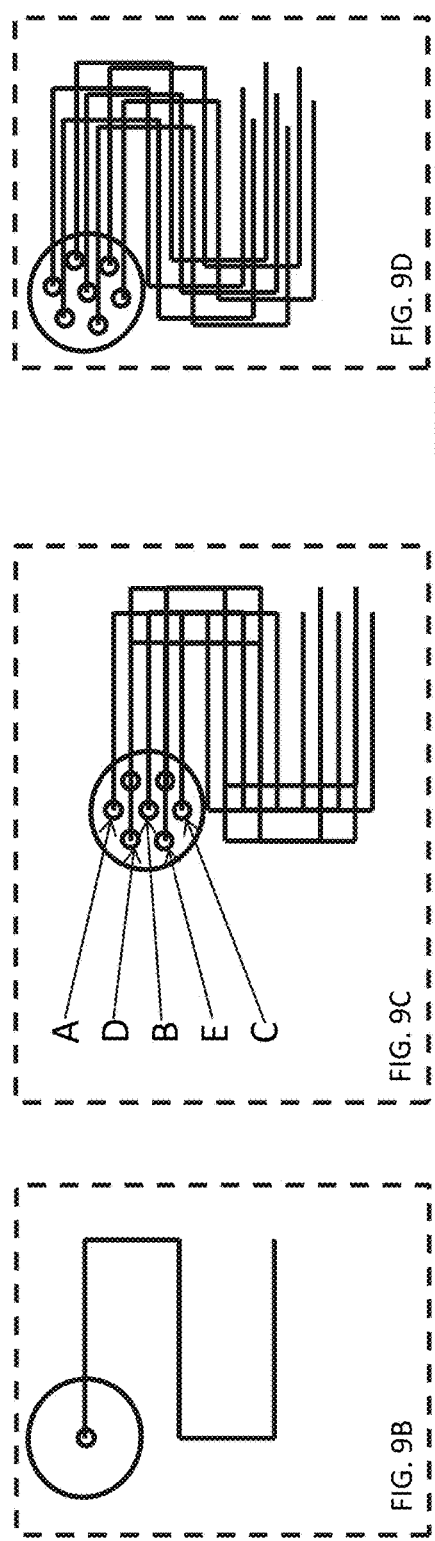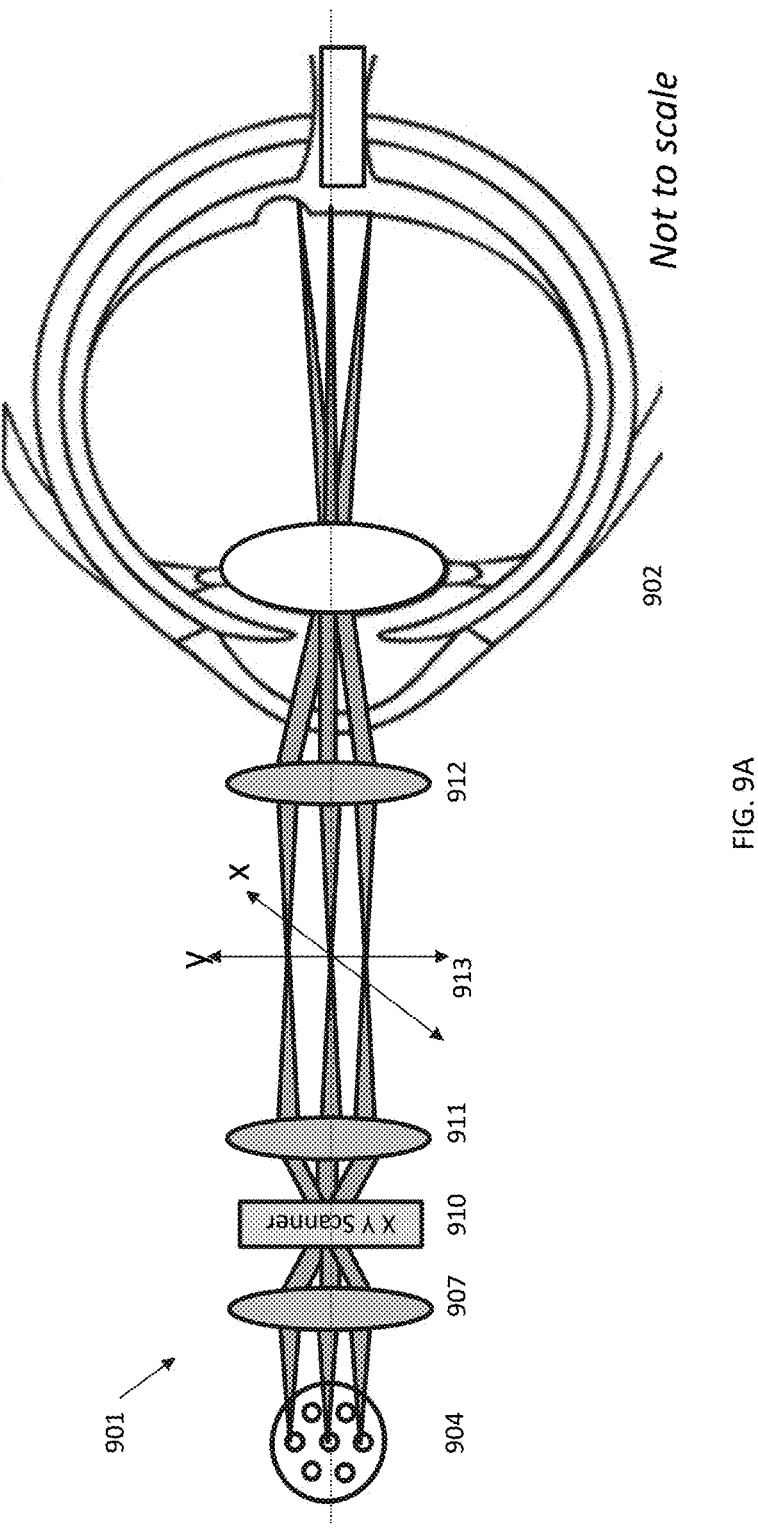

MULTICORE FIBER WITH DISTAL MOTOR

The section headings used herein are for organizational purposes only and should not to be construed as limiting the subject matter described in the present application in any way.

INTRODUCTION

The present teaching relates to medical and non-medical applications for delivering and/or collecting light, and/or performing sensing, and/or performing optical imaging, and/or performing optical therapy of a sample at the distal end of an optical waveguide. There are many medical and non-medical needs for performing optical imaging or sensing of a sample (e.g. human organ or other samples in hard to reach places). Relevant optical properties can include, for example, absorption, reflection, refractive index, birefringence, dispersion, scattering, spectral characteristics, fluorescence, thickness, and other properties. In some embodiments, these relevant optical properties can be determined as a function of wavelength. In addition, the optical properties can be determined at a point, in a small volume, and/or can be spatially or spectrally resolved along one dimension, or multiple dimensions.

Single-mode optical fibers are commonly used to transmit light along a fiber-based optical instrument. They are well suited for use in several embodiments of multicore fiber with distal motor according to the present teaching as they are both inexpensive and flexible. But single-mode fiber by itself has limited capabilities. For example, to perform imaging using a single-mode fiber usually requires scanning the light emitted and/or collected from the single-mode fiber. These known techniques suffer from a variety of significant limitations such as: (1) the endoscopic or other type of probe being too thick and/or not flexible enough to access important regions within the human body; (2) an inability to fit inside existing ports of clinical and non-clinical instruments; (3) the endoscope or optical probe or the system it attaches being too expensive or bulky; (4) the endoscope or optical probe being less reliable than desired; and/or (5) the scanning mechanism introducing optical image artifacts, such as non-uniform rotation distortion. A significant advance over these limitations in prior art fiber-based instruments is needed to open up new clinical and non-clinical applications and to improve performance in existing systems.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The person skilled in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way. Also note for simplicity some of the drawings show beam propagation (e.g. beam divergence) that is not to scale or proportion or exact location within the samples.

FIG. 8 illustrates an embodiment of imaging a human eye using an optical probe system of the present teaching.

FIG. 9A illustrates another embodiment of imaging a human eye using an optical probe system of the present teaching.

FIG. 9B illustrates an embodiment of a scan pattern of a single core of the present teaching.

FIG. 9C illustrates an embodiment of a scan pattern of multiple cores of the present teaching.

FIG. 9D illustrates an embodiment of a scan pattern of multiple cores with a rotation of the present teaching.

DESCRIPTION OF VARIOUS EMBODIMENTS

Figure 1:
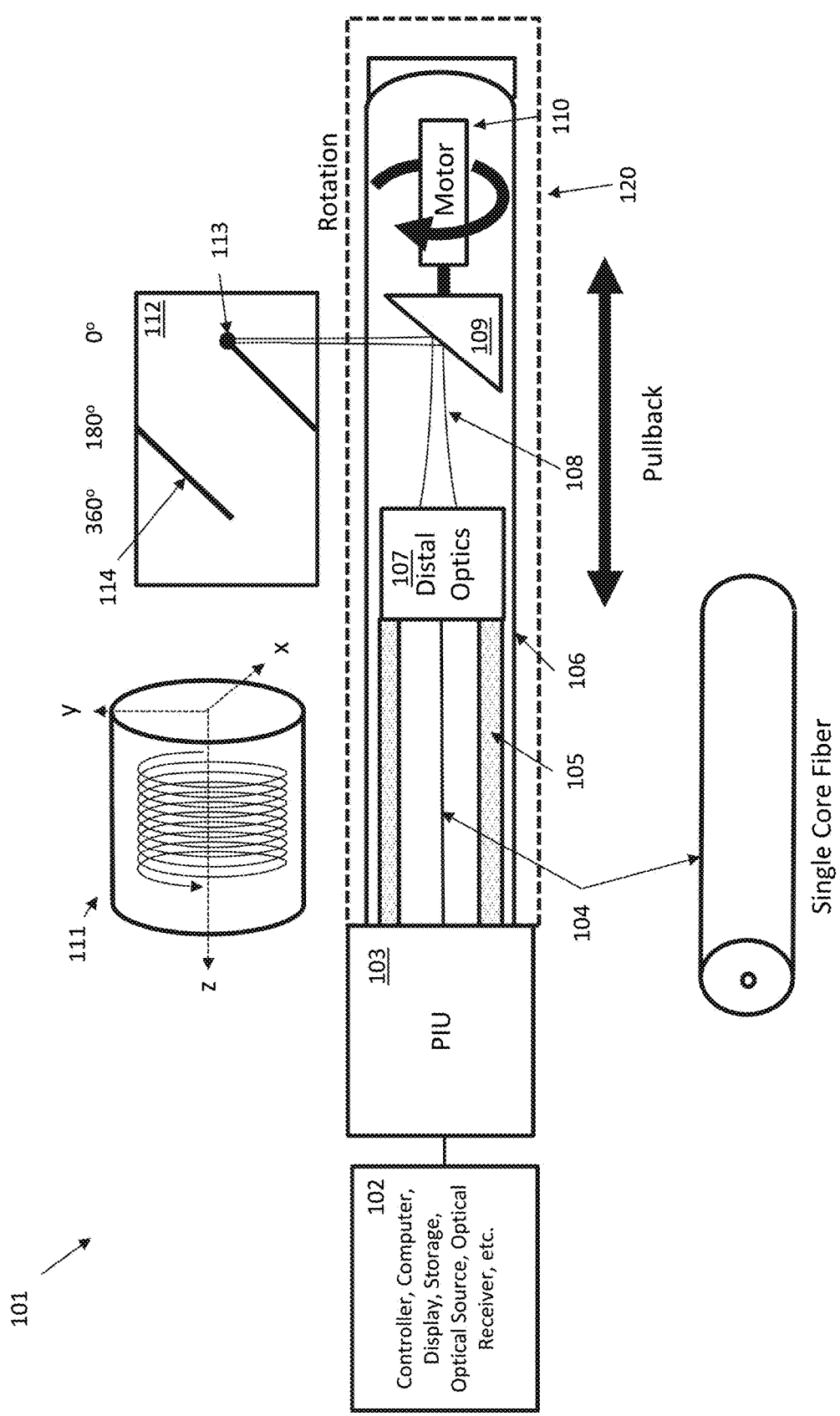
FIG. 1 illustrates a block diagram of a known optical probe system.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teaching can be performed in any order and/or simultaneously as long as the teaching remains operable. Furthermore, it should be understood that the apparatus and methods of the present teaching can include any number or all of the described embodiments as long as the teaching remains operable.

The present teaching relates to the many medical and non-medical applications for delivering and/or collecting light and/or performing optical imaging of a sample in hard to reach places. In this disclosure, the word "light" is intended to be a general term for any electromagnetic radiation, for example, in the wavelength range from ultraviolet to infrared, including the entire visible spectrum. Also, it should be understood that the terms "waveguide" and "fiber" are used interchangeably in this disclosure as an optical fiber is a type of waveguide. It should also be understood that the term "endoscope" as used herein is intended to have a broad meaning to include medical devices such as catheters, guidewires, laparoscopes, trocars, borescopes, needles, and various minimally invasive and robotic surgical devices. In addition, the present teaching is not limited to use in endoscopes but, in fact, has a wide variety uses in fiber-based instruments that are housed in numerous types of packages and apply to a variety of illumination and/or measurement and sensing applications. Examples include ophthalmic imaging apparatus, and surgical and other types of microscopes, tethered capsules, and swallowable capsules, and other devices. A few of such examples are shown in the figures and described herein.

It should be understood that the word "fiber" and the word "core" are used throughout the specification in a somewhat interchangeable manner. In particular, it should be understood by those of skill in the art that when multiple cores are described as embedded in a common cladding, there is an equivalent embodiment with multiple optical fibers, each with a core and a cladding embedded in a second outer common cladding. Such cores could be single-mode, few-mode, or multi-mode optical cores.

There are numerous medical and non-medical applications of optical ranging, sensor, or imaging devices and systems including in cardiology, gastroenterology, pulmonology, laparoscopy, ophthalmology, industrial inspection, NDE/NDT, 3D printing, and LiDAR applications. There are many types of rigid and flexible delivery optical mechanisms including endoscopes, catheters, imaging guidewires, laparoscopes, borescopes, swallowable pill capsules, swallowable tethered capsules, imaging needles, X-Y scanning mirror scanning systems used in ophthalmology, microscope, and other applications and other approaches used to relay optical or other information from a distal location to a proximal location. The description that follows, will most often be described by referring to an optical probe (and occasionally other similar words) but it should be understood that it is equally applicable to these other types of medical and nonmedical instruments. The words "sample", "target," and "tissue" will often be used interchangeably in the text below. Also, often the word "imaging" will be use to describe this invention but it should be understood that this invention is equally applicable to sensors, ranging, therapeutics, interventional, and other optical and electrooptical systems and applications.

Often the word distal motor will be used. This term can reflect a wide variety of types of motors including rotational motors, X-Y scanning galvanometers, translating fibers, translating lenses, MEMs devices, electromagnetic devices, PZT motors, and may other types of motors.

There are many approaches to transferring imaging, ranging, or sensor optical information along an optical probe including utilizing singlemode or multimode fibers, fiber optical bundles, mechanical or electro-optical scanning elements, sets of relay lens, and graded index lenses. For example, the concept of using a single core fiber and a distal spinning motor and a pullback device has been described in the literature and is in common use today in, for example, intravascular and gastrointestinal optical coherence tomography. In general, the term "pullback" may be used to refer to either of both of backward and forward motion of a probe with respect to the sample, unless a direction is specifically indicated.

It should be understood that many of the figures described in the following paragraphs are drawn to illustrate concepts and embodiments of the present teaching, but are not necessarily drawn to scale and often they are simplified drawings omitting known structural and functional elements and/or simplifying optical beam propagation in a way that is known to those skilled in the art. Furthermore, some text descriptions and figures will describe light emanating from a source through a multicore fiber that is directed to and being altered by lenses and other optical elements and impinging on a sample or target. It should be noted by reciprocity that often the reverse path where light is collected on a sample and directed to a receiver is equally suitable even if it is not explicitly mentioned.

FIG. 1 illustrates a block diagram of a known optical probe system 101. The optical probe system 101 includes a system controller 102 connected to a patient interface unit 103. The optical probe system 101 can optionally include a pullback mechanism. The optical probe system 101 includes a single core optical fiber 104, distal optics 107 and a rotating distal motor 110. The single core optical fiber 104 is shown both as part of the probe system 101 and as an expanded view. The optical probe system 101 contains several subsystems. There is an overall system controller 102 that can contain computation (computer), display, storage, power supplies, networking interfaces, an optical source, optical receiver, and various other optical, electrical, and mechanical items. There is a patient interface unit (PIU) 103 that has optical, electrical, and mechanical connections to controller 102. The patient interface unit 103 is also connected to an optical probe 106. There can be various permanent, semi-permanent, and/or attachable/removable optical and electrical and mechanical connections between the controller 102, the PIU 103, and optical probe 106.

There are also structural, optical, and/or electrical connections (not shown) within the optical probe 106 to hold, support and operate the distal folding element 109 and its associated motor 110 and other parts of optical probe 106. They are not shown in any detail for simplicity as they are known in prior art. The optical probe 106 is shown in a simplified view and contains many structural and mechanical and other elements to support the reliable and smooth operation to navigate torturous channels within the human body or in non-medical applications.

The optical probe 106 also contains a single core optical fiber 104. The optical fiber 104 may be enclosed in a structure element 105 to provide additional strength and reliability and/or allow it to be manipulated. For example, the structure element 105 may be a jacket or a buffer or torque coil or other element. At the distal tip of the single core optical fiber 104 is a distal optical element 107 that, in part, controls the properties of the light emitted to and/or collected from the distal target or sample (sample not shown). The distal optical element 107 may include one or more optical elements. Also, a folding element 109 is positioned at the distal end of the optical probe 106. The folding element 109 is connected to a distal rotational motor 110. The folding element 109 may include a mirror (e.g. a fold mirror) or other optical elements.

System controller 102 is electrically and mechanically connected to the motor 110, though this connection is not shown for simplicity. The system controller 102 controls and supports the rotation of the folding element 109. The system controller 102 is connected to the PIU 103. In some embodiments, the PIU 103 contains a pullback motor (not shown) to allow the optical probe 106 to be pulled back, or advanced, along the longitudinal axis (z-axis). In some embodiments, operation the PIU 103 pulls the single core optical fiber 104, distal optics 107, and rotational motor assembly 110 and associated folding element 109 as a unit. In some embodiments, a motor in the PIU 103 can pull the optical probe 106 along an outer concentric sheath 120. In some embodiments, the outer concentric sheath 120 is an outer housing. The outer concentric sheath 120 is only shown conceptually shown by the dotted line in FIG. 1. The outer concentric sheath 120 may be formed by materials surrounding the probe, and may not always be physically part of the probe or attached to the probe. Examples of an outer concentric sheath 120 include within gastrointestinal tissue lumens, coronary arteries, or within accessory port of another optical probe such as an endoscope. In some embodiments, the PIU 103 does not contain a pullback motor and the probe is manually manipulated longitudinally. An example of this would be a system such as a tethered capsule esophageal application.

In operation, system 101 can perform a helical scan or other type of scan within a lumen, solid organ, or other areas within the human body or other medical or non-medical specimens. The helical scan is shown conceptually in inset illustration 111. The relative spacing and pitch of the helix is set by the controller and is in part determined by the ratio of the pullback speed to the rotation speed.

Inset illustration 112 illustrates the unwrapped view. This inset illustration 112 is a diagram of a coordinate-transformed representation of the helical scan illustrated in inset illustration 111. The unwrapped view shows the cylinder shown in inset illustration 112 as cut open along the z axis and thus the helical scan is unwrapped and projected onto the surface shown in the inset illustration 112. The spot 113 shows where the light 108 emitted from the optical probe 106 interacts with a sample (not shown). The light 108 originates from an optical source (not shown) in the controller 102, and propagates to the distal end of the optical probe 106 along single core fiber 104 and then to distal optics 107. After exiting the distal optics 107, the light 108 reflects, or is otherwise directed out of the probe 106 by the folding element 109. The light 108 passes through the transparent outer sheath 120 and impinges on the sample at spot 113. The light may also be collected by the sample at this spot 113. In some embodiments, an optional optical window (not shown) is provided in the optical probe 106 and the light 108 passes through that optical window. A line 114 shows the conceptual path a spot 113 would take along a sample, in the unwrapped view, during a helical scan along the sample. The sample could be, for example, a human coronary artery, vein, bronchial branch, colon, ureter, esophagus, solid organ, etc.

One of the limitations of the known probe system 101 is that the imaging speed can be relatively slow. Increasing the imaging speed can be important in many medical and non-medical applications, such as: (1) to reduce motion induced artifacts from things like breathing, the beating of the heart, or other motion or vibrational disturbances that can corrupt sensor or imaging information; (2) to perform speckle decorrelation angiography; or (3) to minimize the time blood must be flushed out of the coronary artery to allow imaging. Further there has been a tremendous amount of work on intravascular optical coherence tomography systems to perform fast imaging within the coronary artery to locate vulnerable plaques that could rupture and cause a heart attack or other complications, which is useful for performing pre or post assessment of stent placement, etc.

Flushing the blood away from an imaging beam is important for intravascular optical coherence tomography (OCT) but problems can arise during the time the heart is not receiving blood due to this flushing. Similarly, in the esophagus imaging speed is very important because the esophagus is very large and to cover all that area can require tens of gigabytes of data and take many minutes to scan with high resolution. Motion induced artifacts are very difficult to eliminate during this time with the approaches and implementations of prior art systems. This adds to operational costs and procedure and analysis time and makes it extremely difficult to do things like extracting maps of microvessels through speckle decorrelation angiography or Doppler imaging. For example, to do angiography requires high density sampling of tissue which is in contrast to scanning a very large tissue area such as the esophagus. What is clearly needed in cardiovascular, endoscopic, as well as other medical and nonmedical applications is a way to increase the image speed even further and to allow for higher quality images and additional sample information to be obtained such as OCT, angiographic, NIR, fluorescent, or Raman imaging.

One feature of the present teaching is that it increases the speed of imaging or sample information generation as compared to prior art optical probe systems. FIG. 2A illustrates an embodiment of an optical probe system 201 with a multicore fiber 204 of the present teaching. The simplified block diagram of FIG. 2A illustrates a system controller 202 connected to a PIU 203 with a pullback capability. The PIU 203 is connected to an optical probe 206 that contains a multi core optical fiber 204, surrounded by structure element 205, with distal optics 207 at the distal end of the multicore fiber 204. There is a folding element 209 attached to a distal motor 210, that may a rotating motor.

Note that folding element 209 and related items in subsequent figures, e.g. FIGS. 2B-6, is referred to as a "folding element", however it is understood that a wide variety of beam deflector elements are possible. This includes, for example, reflective, transmissive, refractive or diffractive elements, elements with planar surfaces or surfaces with optical power (e.g., for focusing or astigmatism correction) that are anticipated by the present teaching. Also, it should be understood that although a rotational motor 210 is frequently described herein there are other types of motors that can be utilized in embodiments of the present teaching. This includes, for example, motors that rotate back and forth (as opposed to operating continuously in one direction), forward imaging motors, displacement motors that are moving optical elements (e.g. a translating lens system), electrostatic or voice coil motors, and magnet motors that vibrate the tip of the multicore optical fiber, etc. An important feature of the present teaching is the recognition that a predetermined motion of a motor produces a predetermined traversed path of an optical sample spot that can be used to transform collected optical signals from an optical probe system to produce a desired measurement, sensor information and/or image of a sample.

As contrasted to the known optical probe system 101 of FIG. 1, the optical probe system 201 of the present teaching uses a multicore fiber 204 instead of a single core fiber 104. The multicore fiber 204 may be a 7-core fiber, as shown, but other numbers and configurations of cores are anticipated by the present teaching. In some embodiments, the cores are single mode cores, in other embodiments, the cores are multimode cores and, in yet other embodiments, the cores are a combination of single mode and multimode cores. In one embodiment, there are single mode fibers in a common cladding that have no or weak coupling of light as it propagates in the fiber from one core to another. In some applications, it is preferable to use single mode cores, for example in optical coherence tomography. In other applications, multimode fiber or a combination of singlemode and multimode fiber cores can be used to make up the multicore fiber.

There are many possible fiber configurations. In some embodiments, the cores are separate and share a common cladding (as shown in FIG. 2A). In some embodiments, the multicore fiber 204 can contain cores within cores. A notable difference between the known optical probe system 101 of FIG. 1 and the optical probe system 201 of the present teaching is that instead of one light beam between distal optical element and the sample or target, the multicore fiber 204 generates light 208 with seven separate light beams (only three are shown). In various embodiments, the number of beams may or may not be equal to the number of cores, but in general, it should be understood that more than one beam can be emitted from and/or collected by the multicore fiber in the optical probe systems of the present teaching. The optical probe system 201 is used to perform optical measurement of a sample. The sample can be any of a wide variety of elements and can also be referred to as a target, tissue, or other element. Various kinds of samples, targets, tissues and/or other measured elements are described herein as examples, but should not be considered as limiting the inventive subject matter in any way.

The inset illustration 212 shows an unwrapped view of how the optical probe system 201 of the present teaching interacts with a sample. Optical probe systems 201 of the present teaching have optical sample spots. These optical sample spots are spots with particular size, shape, and/or position and each optical sample spot is associated with a particular core in the multicore fiber 204. Specifically, the size, shape, and/or position of a particular spot has a direct relationship to a size, shape, and/or position of a core in the multicore fiber. Depending on the type of measurement, or the application being realized by the optical probe system 201, these optical sample spots may represent illumination from the multicore fiber and impinging on the sample, illumination from the sample collected by the multicore fiber, or some combination of light provided to or collected from the sample.

Each optical sample spot also has an associated path that is traversed across the sample. The path traversed across the sample by a spot has a direct relationship to a motion that is provided by the motor 210 and/or the pullback mechanism provided by the PIU 203. The path is also dependent on the position, size, and/or shape of the core and/or intervening optics.

Continuing with the comparison between the prior art optical probe system 101 of FIG. 1, the optical probe system 201 of the present teaching, referring to the unwrapped representation depicted in the inset illustration 212, instead of one optical spot 113, there is a pattern 215 of seven optical spots including center spot 213 and an outer spot 220. A line 214 shows a conceptual path central spot 113 would take along a sample, in the unwrapped view, during a helical scan along the sample.

Different embodiments will have different patterns 215 of optical sample spots that relate to the pattern of the cores of the multicore fiber. The optical sample spots will have different shapes, different sizes, and different positions that are related to the shapes, sizes and positions of the cores of the multicore fiber. Thus, there is a direct correspondence between an optical sample spot at the sample position and a core of a multicore fiber. The relationship between a shape, size, and/or position of an optical sample spot and a shape, size, and/or position of a core is also dependent upon other factors, including the distal optics 207 and folding element 209. The relationship may or may not be the same for each core and optical sample spot, depending on the intervening optics. However, the relationship is known and predetermined for particular embodiments of the optical probe system 201 and thus, can be used to transform data collected from a sample into useful measurement information. Furthermore, as the pullback and/or rotational motions of the optical probe system 201 progress, each spot will traverse a path that corresponds to a corresponding position, size and/or shape of a core in the multicore fiber. Thus, there exists a predetermined relationship between a motion of the optical probe and a path traversed by the optical sample spots associated with the cores and thus, the relationship can be used to transform data collected from a sample into useful measurement information.

Specifically, as the rotational motor 210 rotates, the folding element 209 and the pullback (or push forward) mechanism in PIU 203 can be activated (or pullback is manually performed), a scan pattern within the lumen (or other sample/target structure) is initiated. This scan pattern 215 can cover more area in the same amount of time, thus improving the speed of obtaining a measurement by the optical probe system. This scan pattern allows additional and/or multiple measurements, sensor, or imaging functions to be performed by the optical probe system 201 at a same time or at different times. As described herein, the pullback mechanism can be a motorized mechanism and/or the pullback mechanism can be a manual mechanism.

Detailed mathematical descriptions of the beam transformations relating the propagation of light from the distal end of the optical probe 206 to the sample (e.g. 212) of FIG. 2A are shown below the Appendix. These transformation calculations serve to aid one skilled in the art to optimize performance for a wide variety of applications. In general, optical probe systems of the present teaching have a predetermined transformation that is based on a configuration of the cores in the multimode fiber and the particular motion provided by the optical probe 206. Using the predetermined transformation, the controller 202 is able to provide a desired optical measurement, sensor, or imaging function based on light that is present within one or more optical sample spots at a sample.

There are numerous design tradeoffs that arise from the combination of motion and multicore fiber illumination and collection in the optical probe system 201 of FIG. 2A. For example, the scan pattern in the presence of rotation of motor 210 and pullback in the PIU 203 is different from the simple helical pattern in the prior art optical probe system 101 of FIG. 1. As compared to the patterns illustrated in inset illustration 111 and inset illustration 112 of FIG. 1, the six circumferential light spots in the pattern 215 illustrated in inset illustration 212 will rotate around the center spot 213 as the motor 210 is rotated. The resulting mathematical relationships are described in detail in the appendix. The effect is conceptually illustrated by the different fill patterns in the spots of pattern 215 in inset illustration 212 and the light lines that illustrate the trajectories of the spots in the pattern 215 in the inset illustration 212. For example, it can be seen that the tightly dotted fill pattern on the target in inset illustration 212 at the 0° rotational motor rotation point, outer spot 220, has rotated 180 degrees relative to the center full dark filled spot once the motor has rotated 180 degrees, translated outer spot 220'.

As a comparison of inset illustration 112 and inset illustration 212 shows, more area can be covered by the optical probe system 201 of the present teaching. Also, the scan pattern that results from the translation of pattern 215 is more complex which allows for a richer data set and a richer measurement and/or sensor and/or image function.

For example, some regions are visited more than once but, at different time periods because, for example, spots associated with different optical cores visit the same sample spot at different times. The fact that the same sample spot (or, in some cases, approximately the same spot) is visited more than once can allow for benefits such as averaging to improve image quality, detection of motion via speckle decorrelation, and many other benefits to extract additional information out of the sample, tissue, or target. Thus, one feature of the present teaching is to configure the shapes, sizes and/or positions of at least two cores in the multicore fiber such that a particular spot on a sample is visited by an optical spot that corresponds to the first core and an optical spot that corresponds to the second core at a different time considering at least one of a relative motion of the optical probe 206 and/or a relative motion of a folding element 209 in the optical probe 206.

There are many design variables that can be used in the optical probe system of the present teaching to improve performance as compared to known optical probe systems that utilize single cores. These include design variables that are suited to specific applications and/or sample types. These also include design variables that are suited to improve a performance of a particular application. Some examples of design variables include the geometry of the multicore fiber, the number of cores, the size of the cores, and/or their relative spacings. These variables can be used, for example, to change the shapes, sizes, and positions of the resulting optical sample spots as well as how the optical sample spots may change as a result of probe motion. Some or all of the cores can be single mode cores. Some or all of the cores can be multimode. In addition, some or all of the cores can be few-mode cores. The various different types of cores will affect the amplitude and phase(s) of the provided and/or collected light that propagates in the cores.

Another important design variable is the imaging properties of the distal optics and how the light emitted and/or collected from the multicore fiber is imaged onto and/or collected from the sample. These designed imaging properties will affect, for example, spot sizes, focal plane positions, spot shapes of the optical sample spots. In some embodiments, a different imaging function is provided for different cores. In some embodiments, the same imaging function is provided for different cores. In some embodiments, a single imaging function is performed on multiple cores.

Another important design variable is the angle of the folding element 209 normal relative to the longitudinal axis of the optical probe. The embodiment of FIG. 2A shows the folding element 209 arranged to deflect the beam approximately 90 degrees but the mirror normal angle can be more or less in various configurations.

Another important design variable is the optical properties of the folding element 209, which can be embodied in as a reflective or a refractive device. The folding element 209 can also have a flat surface or have optical power that provides focusing properties.

Another important design variable is the relative speed of the rotational motor compared to the pullback motor. The speed of rotation and/or speed of pullback determine the traversed paths for the optical sample spots. Thus, these speeds impact the transformations that are utilized by the control system 202 to produce a measurement result from a collection of light in an optical sample spot by the cores of the multimode fiber 204 of the present teaching.

For example, in one embodiment, it is desirable to have minimal gaps in areas where the sample is not imaged. Referring to the inset illustration 212 in the example of FIG. 2A, the pullback rate can be decreased and/or the optical spot sizes on the sample can be made bigger, or the radius of the six spots surrounding the central spot 213 can be made bigger. The result is less imaging gap along the tissue, or more cores can be added to the multicore fiber 204. Thus, a rate of motion can be provided that provides a desired image gap along a sample. Also, a core size of at least two cores can be provided that provides a desired image gap along a sample. Also, a number of cores can be provided that provides a desired image gap along a sample.

The distal optics 207 is used to shape and direct the light from the distal end of the multicore fiber 204. A variety of lenses and lens positions with respect to the core(s) in the multicore fiber can be used to direct the light from the distal tip of the multicore fiber to and from the sample. For example, the distal optics can include single element lenses, multielement lenses, lens groups, lens-let arrays, prisms and lenses, ball lenses, singlecore and multicore fiber lenses, and/or other optical elements. In one embodiment according to the present teaching that is particularly well-suited to single-mode cores, the distal optics includes 3D printed optics on the distal tip. The 3D printed optics can include a beam expansion region positioned between the multicore fiber distal facet and a distal optical-powered lens surface. This allows light from each core to expand via diffraction in the beam expansion region. The beams expand a small amount. In some embodiments, the beams do not overlap. In some embodiments, the beams overlap a small amount. The use of an expansion region allows, for example, larger beam diameter and thus results in longer focal lengths of optical beams provided by the cores. The expansion region also accommodates an angled facet at the distal end of the multicore fiber 204 so that this exit facet has minimal undesirable back reflections.

In some embodiments, 3D printed individual small lenses (or lenslets) are placed in the path of each core to focus the light onto, and/or collect light from, the distal target (e.g. coronary artery or esophagus). There are many possible combinations of lenses and associated fiber cores. In other embodiments, lenslets are not used and a single lens or lens group is used (an example embodiment of this is discussed below) to focus light from multiple cores.

FIG. 2B illustrates an embodiment of a portion of an optical probe system 251 with a non-planar folding element of the present teaching. The embodiment of FIG. 2B illustrates a non-planar folding element 209' that collects light from the distal end of a multicore fiber with angled distal facet 204'. In this embodiment, the distal optical element can be eliminated (or simplified) and the folding element 209' comprises a mirror that both redirects the light and provides the focusing of the light by having an appropriate non-flat surface (e.g. a concaved surface). For simplicity, only one emitted beam from the multicore fiber is shown as 208', but it should be understood that in most embodiments there is a light beam emitted and/or collected from each core of the multicore fiber. This implementation is also a very substantial improvement over the prior art, even if only one fiber core is used as illustrated in FIG. 2B. Such a configuration eliminates the more complex distal optics and, consequently is more compact and easier and less expensive to manufacture. In some embodiments, the output facet of the multicore fiber is cleaved a right angle to the axis of the fiber. In the embodiment illustrated in FIG. 2B, the distal end of a multicore fiber with angled distal facet 204' is cleaved at a sufficient angle (e.g. seven degrees for a 1310-nm singlemode fiber core) such that this implementation can have very little back reflection from the distal tip area and mainly collect light from the target. This feature is important in high sensitivity optical imaging and sensing applications like OCT, NIR, and other modalities. There are a variety of methods that can be used to accommodate the slight deviation of emission angle relative to the multicore fiber axis due to the angled facet (dictated by Snell's law). These methods include offsetting the center of the fiber relative to the axis of the probe or motor, tilting the distal tip of the multicore fiber at an angle, and adding additional optical elements. It can also be possible to provide some astigmatism correction from the aberration effects of the outer transparent sheath of the optical probe (not shown) by adding additional distal optical elements in the light path or preferably in the design of non-planar surface of fold mirror 209'. The correctable aberration can also be caused by an exit window around the exit points of beams 208'.

Having a reliable indicator of angular position of the distal motor 210 can be an important factor, especially in high speed small motors. This angular position is needed in order to reliably know where the beam is on the target. For some motors, the electrical signal that drives the motor can be a reliable indicator of the position. For other motors a once-per-revolution or multiple-pulse-per-revolution angular encoder connected to the motor can aid in more precise angular location identification. Another method suitable for many endoscopic and other applications is to place fiducials on an outer concentric sheath or housing (not shown). The fiducials effect the optical beam transmitted and/or received by absorbing, scattering, or altering the beam propagation through the fiducial. Then, using signal processing, the adjacent angular scans can be aligned to the fiducials by lining them up after imaging reconstruction. Another approach is to use information from the target itself such as the inherent speckle. Non-uniform rotational distortion (NURD) is known to be correctable using these and other approaches. Similar approaches can be used in the longitudinal direction (e.g. pullback), however, it is easier to have a precise encoder on the longitudinal motor as there is typically more room in the area of the PIU 203. For X-Y scanning galvanometers, it is common to have encoders as a reliable indicator of mirror position and often feedback loops are incorporated in the drives to ensure minimal error between commanded position and actual mirror position.

While the descriptions provided herein generally refer to illumination that emanates from the probe and is projected toward the sample, it is understood that the system according to the present teaching may operate with all or some light emanating from the sample and the optical probe acting as a collection system. Combinations of these different directions are also anticipated. The principles of operation of the present teaching are generally reversible, and the probe can operate in either and/or both directions, as understood by those skilled in the art.

One feature of the present teaching is that numerous types of optical imaging, sensing, or ranging applications that can be implemented by the methods and apparatus of the present teaching. Referring to FIG. 2A, for example, the system controller 202 can produce time domain, spectral domain, or swept source optical coherence tomography or other types of interferometric imaging, near infrared imaging, spectroscopic imaging, diffuse wave imaging, Raman imaging and sensing, and fluorescence imaging or sensing, and various combinations thereof. In some embodiments, different cores, or sets of cores implement different types of application. In other embodiments, all or most cores are used together to support a particular application.

Figure 3:
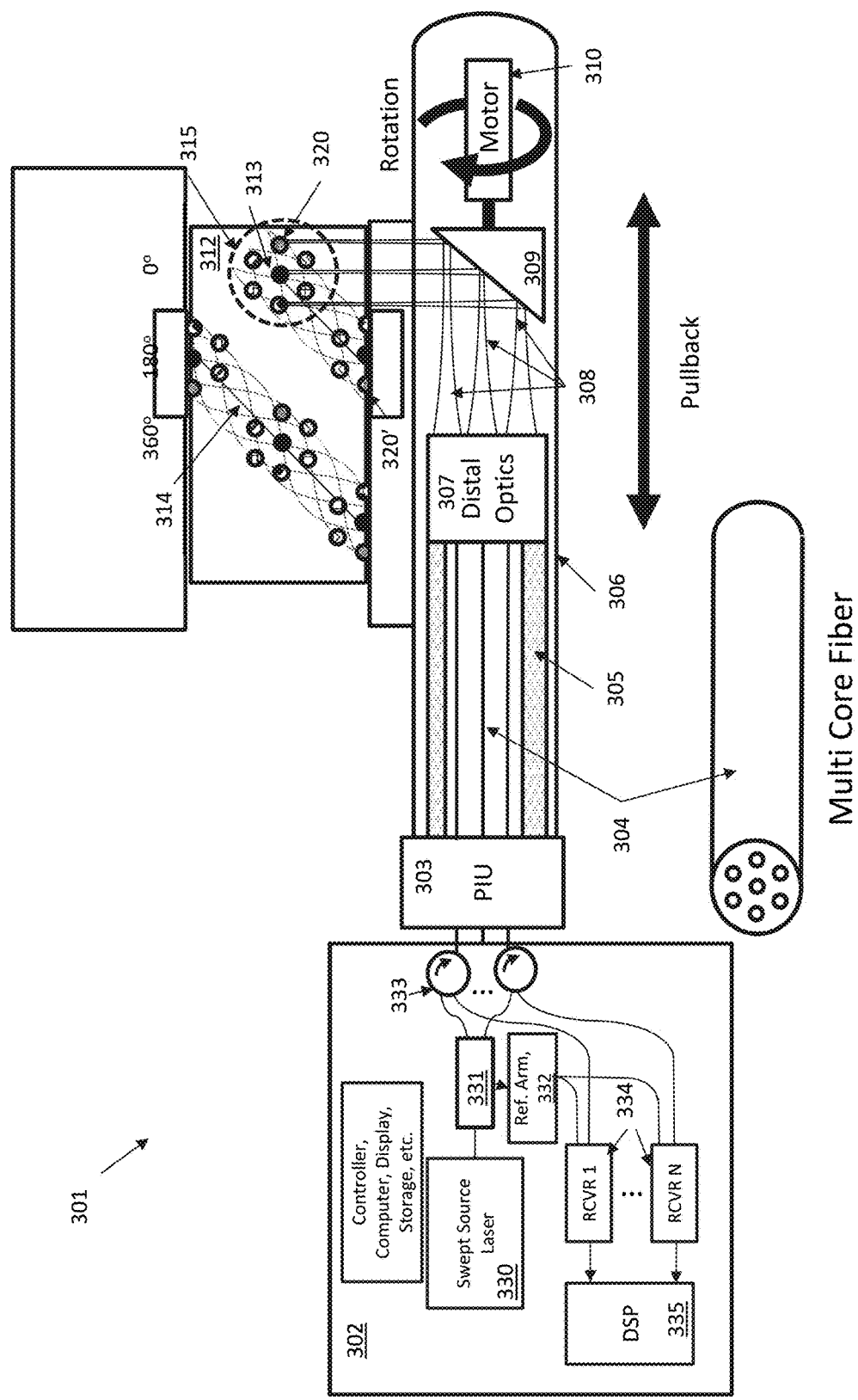
FIG. 3 illustrates an embodiment of an optical probe system with a multicore fiber that implements optical coherence tomography imaging of the present teaching.

FIG. 3 illustrates an embodiment of an optical probe system 301 with a multicore fiber 304 that implements optical coherence imaging of the present teaching. The optical probe system 301 includes a system controller 302 connected to a patient interface unit 303 with a pullback capability, an optical probe 306 containing a multicore optical fiber 304 surrounded by structure element 305 with distal optics 307, and a rotating distal motor 310. The optical probe system 301 uses swept source optical coherence tomography with parallel receivers 334. A swept source laser 330 is coupled to the PIU 303 and the system controller 302 is configured such that the optical probe system 301 implements an optical coherence (SS-OCT) imaging system. An inset illustration shows the unwrapped view of the trajectory of the pattern of spots 315 associated with the cores of the multicore fiber 304 during a helical scan caused by a combination of the pull back of the probe 360 and the rotation of the folding element 309 by the motor 310. A line 314 shows a conceptual path central spot 313 would take along a sample, in the unwrapped view, during a helical scan along the sample.

The control system 302 is positioned at the proximal end of the optical probe and contains all the control and computation, display, and other functions that are customary in SS-OCT systems. In particular, the control system 302 contains a swept source laser 330 that is optically coupled to a beam splitter 331. The beam splitter 331 directs light to both a reference arm unit 332 and to each of a plurality of circulators 333. Each circulator 333 is optically coupled to one single mode core of the multicore fiber 304. In some embodiments, one or more of the cores that are optically coupled to a circulator 333 is a few-mode fiber. Each circulator is also coupled to a receiver 334. Optionally, beam splitters may be used instead of circulators 333. The reference arm unit 332 may contain an optional adjustable delay to approximately match the optical path length in the sample and reference paths as is known in the art of SS-OCT. Alternatively, it is possible to use one of the cores in the multicore fiber 304 as some or all of a reference path. If one of the cores in the multicore fiber 304 is used as some or all of the reference path, a reflection from at or near the distal end reference core of the multicore fiber 304 can serve as part of the reference path. One feature of this configuration is that implicitly the length and dispersion are nearly matched between the reference and sample paths within the multicore fiber 304, which makes manufacturing easier since tight tolerances on length of the probe 306 are relaxed.

In the SS-OCT optical probe system 301 of FIG. 3, there are shown multiple receivers 334 that detect light in parallel. Although not shown in FIG. 3, it is possible to use a single receiver to receive the reference signals and the light that emerges from the circulators 333. In some embodiments, an optical switch is used to pass light from the multiple cores to the receiver. In some embodiments, one or more time delays are provided between the light that emerges from the circulators and the receiver and, the different optical channels are detected using distinct delays in each sample path (or reference path) that emerges from the multicore fiber 304. Each different optical channel can be processed separately using the fact that each will have a distinct electrical frequency band. There is a digital signal processor 335 connected to the receivers (or receiver) to extract imaging and other information.

Cost and/or size are important in virtually all applications. To minimize cost and/or size, it can be highly beneficial to use one or more photonic integrated circuits (PIC) to realize many of the optical functions shown in the diagram of the control system 302. For example, in embodiments in which the receivers 334 are coherent receivers, it possible to put multiple coherent receivers, with associated optical waveguides and integrated photodetectors on a single PIC. Many other combinations of optical functions can be combined on a PIC to realize any of size, cost, complexity and/or performance advantages.

In some embodiments, it is possible to have an additional motor translating (not shown) the distal end of the multicore fiber 304 shown in optical probe 306. It is known in the art that the lateral translation of a fiber relative to the axis of a lens can cause light emitted scan relative to the axis of the lens. It is also possible to translate a lens and have a fixed fiber. One feature of using an additional motor in a multicore fiber configuration is that multiple receivers can be used to dramatically increase the speed of acquisition. This is because there is an increase in area coverage and the potential of multiple receiver configurations. Such a configuration also allows for the collection of additional information such as light emitted from one fiber being collected in another fiber. It should be understood that the use of an additional motor is not limited to the embodiment of FIG. 3, and applies generally to various embodiments described herein.

It should also be understood that although FIG. 3 is described with respect to a swept source OCT system, it is equally applicable to implementation of a spectral domain OCT system or other types of optical systems. Also, an alternative embodiment described later in connection with the description of FIG. 10 uses a single receiver and a fast optical switch. This embodiment is described with respect to a forward X-Y scanner embodiment but such an embodiment is equally applicable to an optical probe like implementation with a rotating distal motor such as the configuration shown in FIG. 3.

Figure 4:
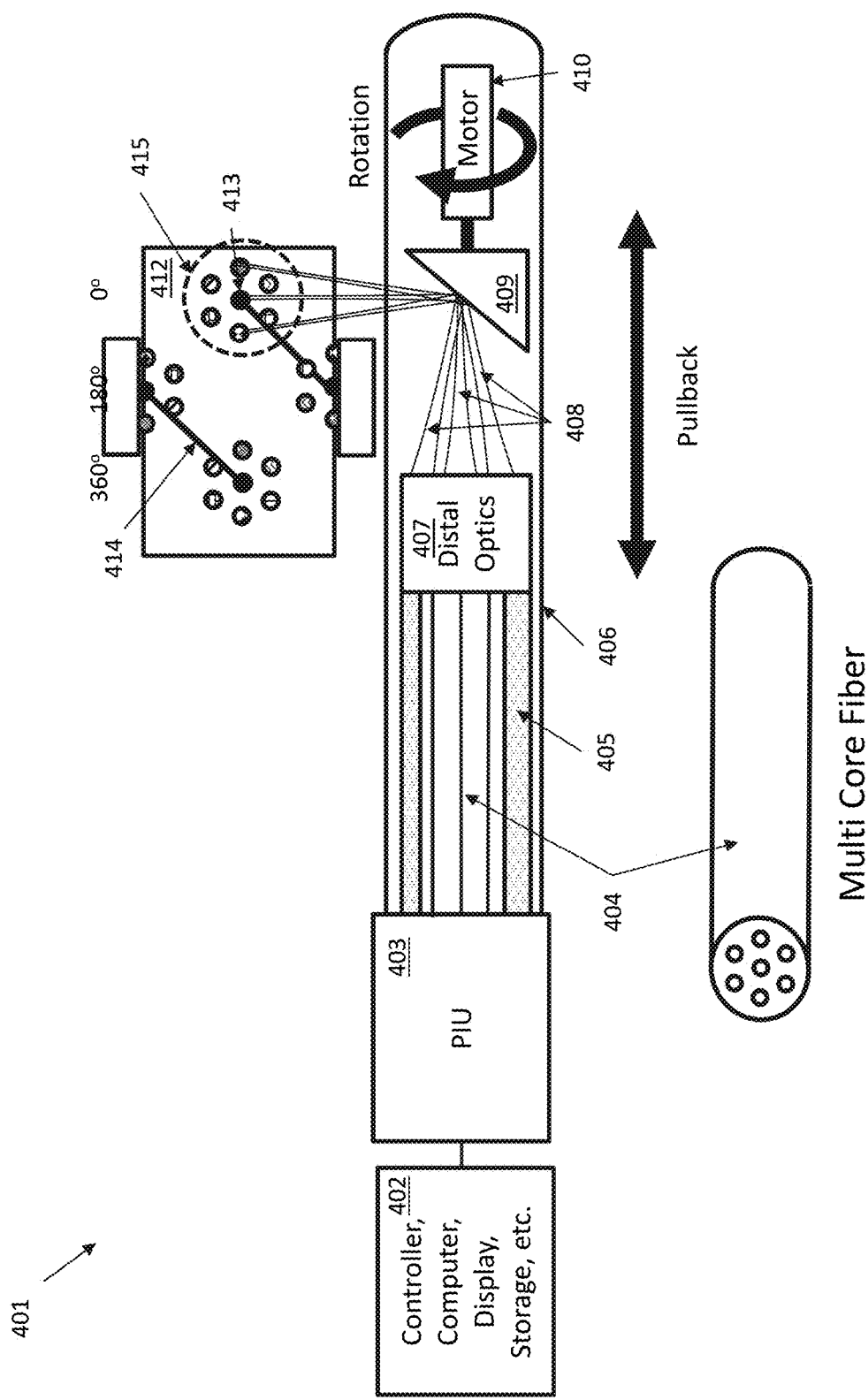
FIG. 4 illustrates an embodiment of an optical probe system with a multicore fiber that converges optical beams at a central axis of a rotating motor of the present teaching.

FIG. 4 illustrates an embodiment of an optical probe system 401 with a multicore fiber 404 that converges optical beams 408 at or near the central axis of a rotating motor 410 of the present teaching. The optical probe system 401 includes a system controller 402 connected to a patient interface unit 403 with a pullback capability. An optical probe 406 contains a multicore optical fiber 404, surrounded by structure element 405, with distal optics 407 and a rotating distal motor 410. The distal optics 407 emits and/or collects light that converges near the center axis of the distal motor. The light 408 emitted (or impinging) onto the cores of multicore optical fiber that are positioned off the central axis of the multicore fiber follows a path with a slight angle relative to the longitudinal axis of the optical probe 406 such that the various light beams converge near, or even at, the center of the rotating folding element 409. The folding element 409 may be a flat mirror angled at 45 degrees from the longitudinal axis of the probe in some embodiments. The fact that the beams converge near, or event at, the center of the rotating folding element 409 has the advantage of allowing the folding element 409 to be slightly smaller, than, for example embodiments with more space between optical beams associated with different cores at the folding element surface. A smaller folding element means that the folding element 409 has the potential to spin at even high speeds and the optical probe 406 can fit into smaller lumens or medical endoscope access ports.

In some embodiments, the distal optics 407 is placed approximately one focal length from the center axis of the folding element 409 and the distal facet of the multicore fiber 407 is imaged into the sample tissue with a desired inverted magnification to achieve the desired spatial coverage, the resolution, and the depth of field. In some embodiments, the distal optics 407 is placed approximately one focal length from the center axis of the folding element 409 and the distal facet of the multicore fiber 407 is imaged into the sample tissue with a desired non-inverted magnification to achieve the desired spatial coverage, resolution, and depth of field. Inset illustration 412 illustrates a diagram of a coordinate-transformed representation of a helical scan. A line 414 shows a conceptual path a central sample spot 413 would take along a sample, in the unwrapped view, during a helical scan along the sample.

Detailed mathematical descriptions of the beam transformations relating the propagation of light from the distal end of the optical probe to the sample, as shown in the inset illustration 412, are shown in the appendix. These calculations illustrate how the optical probe system 401 performs and can be optimized for a wide variety of applications. Specifically, these calculations help to illustrate how the relationship between a shape, size and/or position of a core in the multicore fiber 404 and a shape, size and/or position of an optical spot at the sample have a known relationship. The calculations also illustrate how, as the pullback and/or rotational motions of the optical probe system 401 progress, each optical spot will traverse a path that corresponds to a position of a core in the multicore fiber. Using these known relationships between cores, optical sample spots, and traversed paths, a mathematical transformation can be performed in the controller 402 that produces sample information.

A numerical example of the embodiment of the optical probe system 401 illustrated in FIG. 4 including a multicore fiber that has been commercially manufactured follows. The core-to-core spacing is approximately 37 μm and the mode field diameter at the exit facet of the multicore fiber is about 10 μm at 1310 nm. A common size of lumen in human coronary arteries vessels can be ~4 mm in diameter. A common full-width-half-maximum (FWHM) beam diameter at focus in the sample tissue in swept-source intravascular OCT systems is ~25 um. This gives a reasonable Rayleigh range (or confocal parameter) to measure the SS-OCT A-scan range over. Thus, having the distal optics 407 arranged to implement a magnification of ~2.5 can be useful and achieved with relatively simple, small, and low-cost optical elements. Such optics translates the ~10 um mode field diameter at the fiber distal facet to a ~25 um spot size near the vessel wall. In this simple example, the spot-to-spot spacing of the spot pattern 415 would be approximately 37×2.5=92.5 um. The distances from the distal fiber facet to the lens plane, the lens focal length, and the distance from the lens plane to the image (e.g. location of spot 413) are all governed by the lens equation (and more advanced versions of that equation) as is known in the art, and can be set by the desired application. For example, one application is imaging with in a coronary artery of ~4 mm diameter or imaging within a balloon inflated esophagus or imaging with a swallowable or tethered capsule ~20 mm in diameter.

Note that it can be beneficial to have this spacing denser and to achieve fiber cores more closely spaced than 37 um to allow a tighter cluster of spots on the artery wall. If the core-to-core spacing in the multicore fiber 404 is too close, the light from one core will start to couple or leak into the adjacent core. Many factors influence this including the index of refraction profile in the cores and cladding and the wavelength of light, but generally cross talk start to happen in a significant way as the spacing gets near the mode field diameter. But because the length of the multicore fiber 404 in endoscopic applications (~1-2 m) is far less than that for typically telecommunication applications (10 m to many km), the cores can be more closely packed than in telecommunications.

In some embodiments, it is possible to use a spinning or fixed wavelength dispersive device such as a grating in the folding element 409. It should be understood that such a dispersive device can be used in other embodiments of the present teaching as well. This produces a spatially separated set of patterns 415 at the sample, where each spatially separated pattern 415 is at a different wavelength. A wavelength dispersive device allows the emission angle of the optical beams to be scanned via wavelength tuning of an optical source (or spatially dispersed if a broadband source is used instead of a tunable source) in the system controller 402. This is analogous to a spectrally encoded confocal microscopy (SECM) and other methods of wavelength scanning. In these embodiments, the source in the system controller 402 includes a wavelength tunable (or broad bandwidth) optical source. The process of wavelength scanning from a diffraction grating or other wavelength dispersive device is understood by those skilled in the art. Applying the wavelength scanning by including a dispersive element in rotating folding element 409 in combination with multicore fiber 404 allow for much greater coverage of tissue in a given amount of time or provide other valuable tissue information.

The equations for the beam translation described in detail in the Appendix are based on non-dispersive reflective devices. However, these equations can be modified in a straightforward manner by those skilled in the art to include the grating properties that govern light diffraction by a dispersive element, such as a grating, in the folding element 409.

Figure 5:
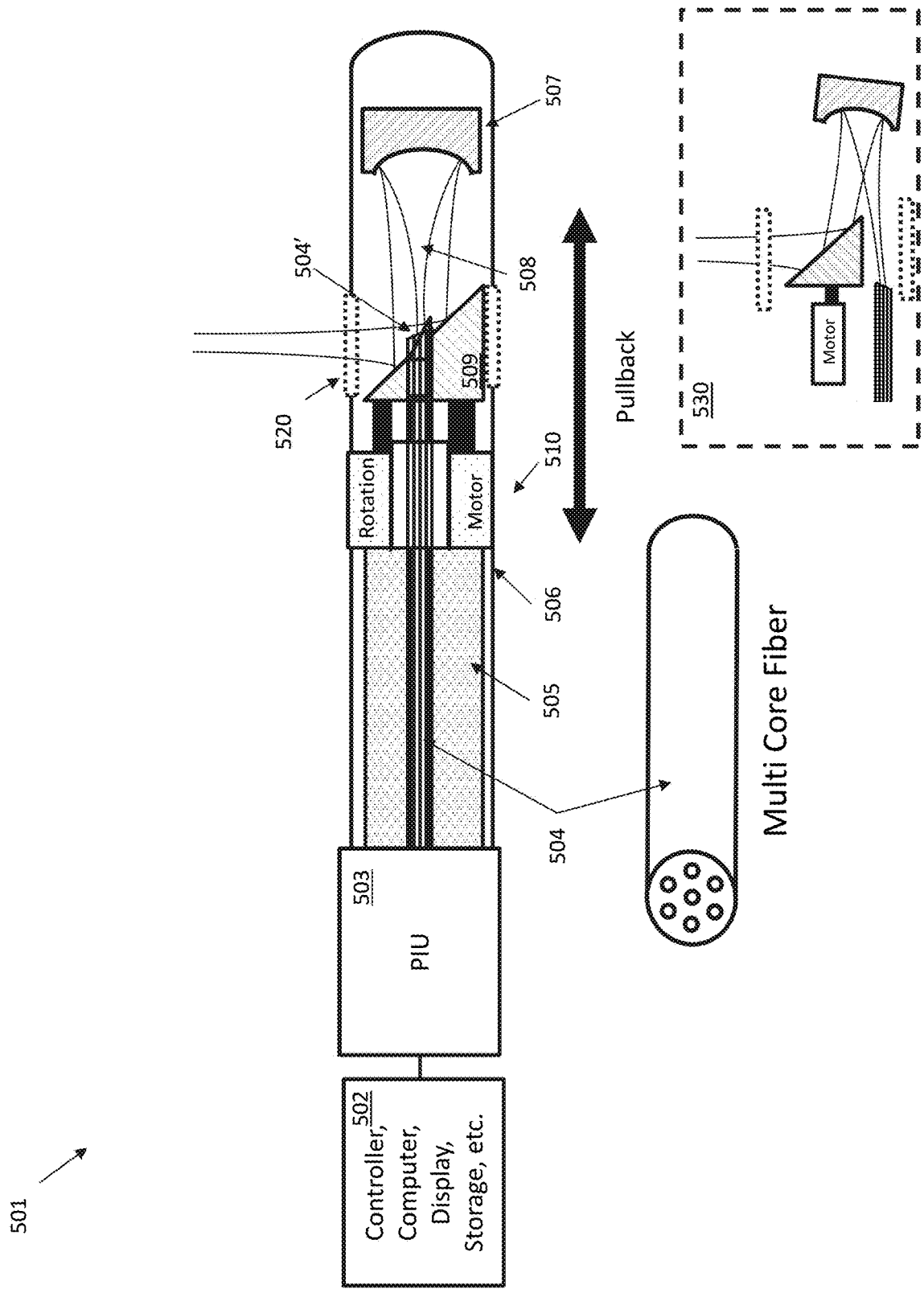
FIG. 5 illustrates an embodiment of an optical probe system with a multicore fiber and a hollow motor of the present teaching.

FIG. 5 illustrates an embodiment of an optical probe system 501 with a multicore fiber 504 having a hollow motor 510 of the present teaching. The optical probe system 501 includes a system controller 502 connected to a patient interface unit 503 with a pullback capability. An optical probe 506 that contains a multi core optical fiber 504 with distal optics 507 and a rotating distal motor 510. The motor 510 and the folding element 509 are hollow to allow a fiber and/or light to pass through the motor 510 and/or the folding element 509 to the distal end of the probe 506 where distal optics 507 are positioned. Thus, in this configuration the hollow motor 510 and hollow fold mirror 509 are followed by a reflective and concaved distal optical element 507.

For simplicity, the light 508 emitted (or collected) from only one core of the multicore fiber 504 is drawn but it should be understood that in some embodiments there may be more than one core in the multicore fiber and more than one light beam emitted and/or collected. It should be understood that some optical sample spots associated with a core may propagate in the same optical beam (this can be viewed as a beam within a beam), so a number of beams is not necessarily the same as a number of spots. As previously described, the distal facet of the multicore fiber can be cleaved or polished at an angle to form angled distal facet 504'. As described herein, the outer sheath of probe 506 can be optically transparent. Alternatively, in some embodiments a transparent window shown in the dotted line of 520 can be utilized. One advantage of this approach is that there are fewer or, in some embodiments no, electrical or mechanical structures in the path of the optical beams as they scan/rotate around the circumference of the optical probe. Such structures can cause outages in the imaging or sensing capability of the system. In some embodiments of the earlier diagrams there are electrical and/or mechanical connections from the controller or PIU to the distal motor that can cause signal dropouts as the light beam sweeps through those areas.

An alternative embodiment of a configuration for the elements at the end of probe 506 is shown as inset illustration 530. This embodiment still has a distal optic 507, and can function without having a signal dropout from sweeping thorough electrical or mechanical elements but does so without having a hollow motor like 510 or hollow prism like 509 as shown conceptually within the inset illustration 530. Here the multicore fiber is offset from the motor and the optical path from the multicore fiber light emission (or collection) angle. The distal optic, and the fold mirror are arranged so that light freely propagates with no electrical or mechanical impediments.

As described herein, the folding element can be a wavelength diffractive reflective element that implements wavelength scanning in combination with rotational scanning and/or pullback scanning, instead of the reflective surface shown in folding element 507. The combination of multicore fiber, with rotational scanning, and wavelength scanning can allow for even more rapid scanning since it is possible to create tunable lasers that can run at speeds in excess of 1 MHz.

Figure 6:
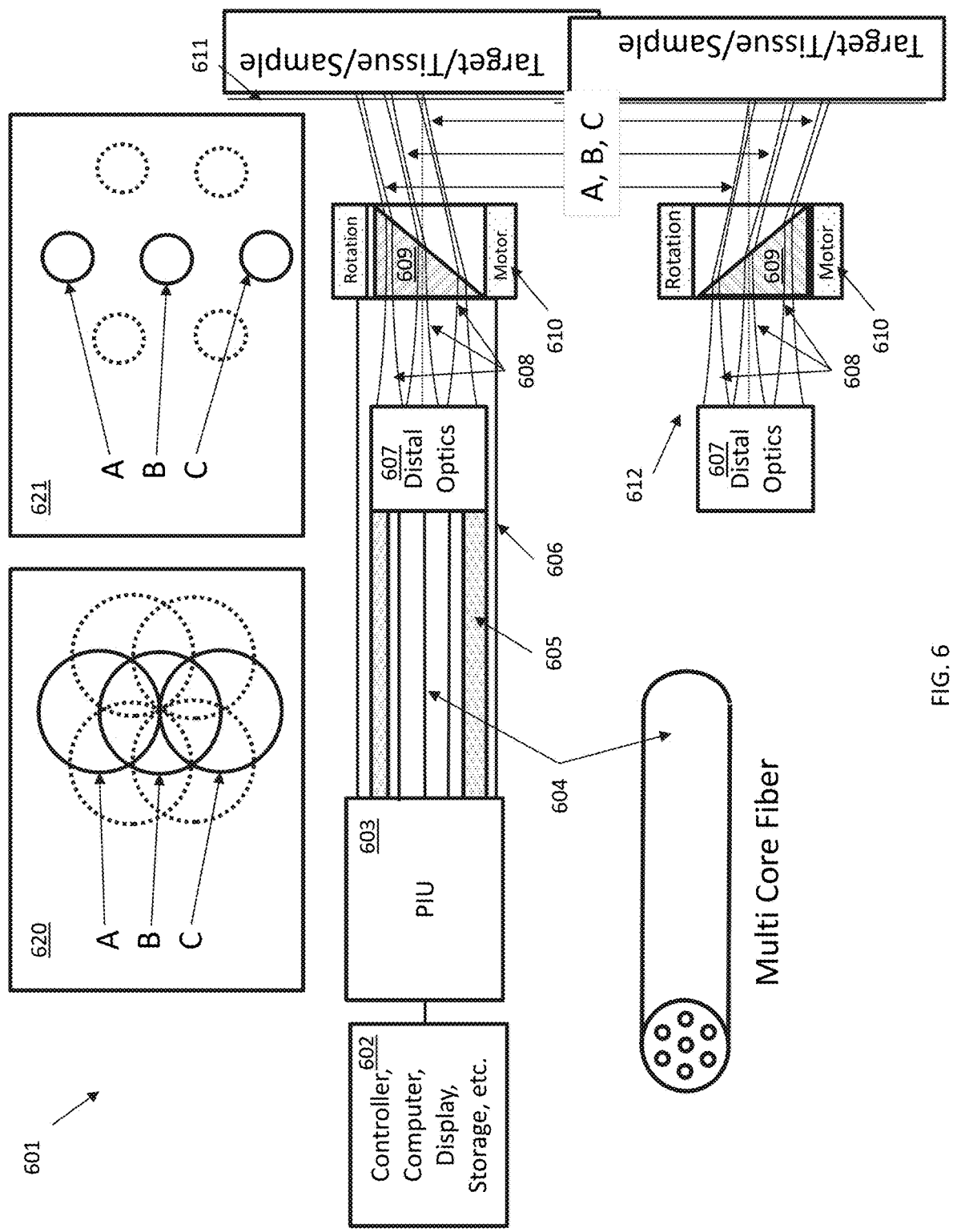
FIG. 6 illustrates an embodiment of an optical probe system with a multicore fiber and configured for forward imaging of the present teaching.

FIG. 6 illustrates an embodiment of an optical probe system 601 with a multicore fiber 604 configured for forward imaging of the present teaching. The optical probe system 601 includes a system controller 602 connected to a patient interface unit 603. In various embodiments, the PIU 603 may or may not include a pullback unit. An optical probe 606 contains a multi core optical fiber 606 that is optically coupled to distal optics 607 and a rotating distal motor 610 that rotates a folding element 609. This optical probe system 601 is configured to allow forward imaging to a sample 611. In various embodiments, the sample 611 may be a tissue or a target.

The optical probe system 601 uses a rotating distal motor 610 containing a folding element 609, which in some embodiments is a prism. The folding element 609 for these embodiments of forward imaging are generally transparent to allow the optical beams 608 to pass through the element 609. In the embodiment shown, the folding element 609 is bending the beams upward. Inset illustration 612 partial view shows the folding element 609 in the end of the probe 606 turned by 180 degrees when the folding element 609 is bending the beams 608 downward. Letters A, B, C refer to beams as they exit the folding element 609 from a side core, the center core, and another side core, respectively. In contrast to some of the configurations shown herein, this forward imaging pattern does not have the outer light beams emitted from the probe 606 (such as A and C) rotating 360 degrees around the center light beam B, but rather each light beam rotates in its own approximately circular fashion. Inset illustrations 620 and 621 show examples of the circular paths traced by the centers of the optical sample spots at the sample plane. Each optical sample spot in the optical sample spot pattern traces an approximately circular loop and those loops may (620) or may not (621) overlap and, if they overlap, the degree of overlap may vary, depending on dimensions and optical elements involved for the particular application. Thus, the path traversed across the sample is a circular loop. The center beam, if any, behaves similarly to all others. The solid circles illustrating the paths of the optical sample spots shown in inset illustrations 620 and 621 correspond to the beams A, B, C shown in the other views of FIG. 6, and the dotted circles correspond to beams from other cores propagating beams that are not shown in the other views.

The embodiment shown in FIG. 6 illustrates how different paths for optical sample spots can be achieved using different configurations of optical and mechanical elements in the optical probe system 601. Optical probe systems of the present teaching rely on the predetermined paths of the optical sample spots being used in a transformation of collected optical data to produce measurement data for particular applications.

While not illustrated in FIG. 6, it is understood that in some embodiments, the optical sample spots at the sample 611 may also have a size shape and/or position that are related to the size, shape and/or position of the core associated with that optical sample spot. These attributes of the illumination and/or collection pattern can also be used as part of the transformation of the collected data in rendering a desired measurement at the output of the optical probe system 601 as described herein.

As described herein, the PIU 603 may or may not have a pullback motor, but a known relationship exists between any pullback motion of the probe 606 and a path traversed by an optical sample spot associated with a core in the multicore fiber 604 and/or a size, shape and/or position of an optical sample spot at the sample 611.

As mentioned above, it is possible to use a wavelength diffractive element in the folding element 609 described in connection with FIG. 6, with or even without a rotating motor.

Various embodiments of the multicore fiber with distal motor according to present teaching have been described herein in connection with FIGS. 2A-6. It should be understood that various features described in connection with a particular embodiment are not necessarily limited to that embodiment. For example, embodiments that are described in connection with reflective optical elements can also be realized with transmissive optical elements while still practicing the associated aspects of the present teaching. Similarly, embodiments that are described in connection with transmissive optical elements can also be realized with reflective optical elements while still practicing aspects of the present teaching. Various embodiments may operate with light that is supplied to a sample and/or light collected from a sample while still practicing the present teaching. In general, it should be understood that the various embodiments described herein may be used in connection with various measurement and/or sensing and/or imaging applications while still practicing of the present teaching.

Figure 2:
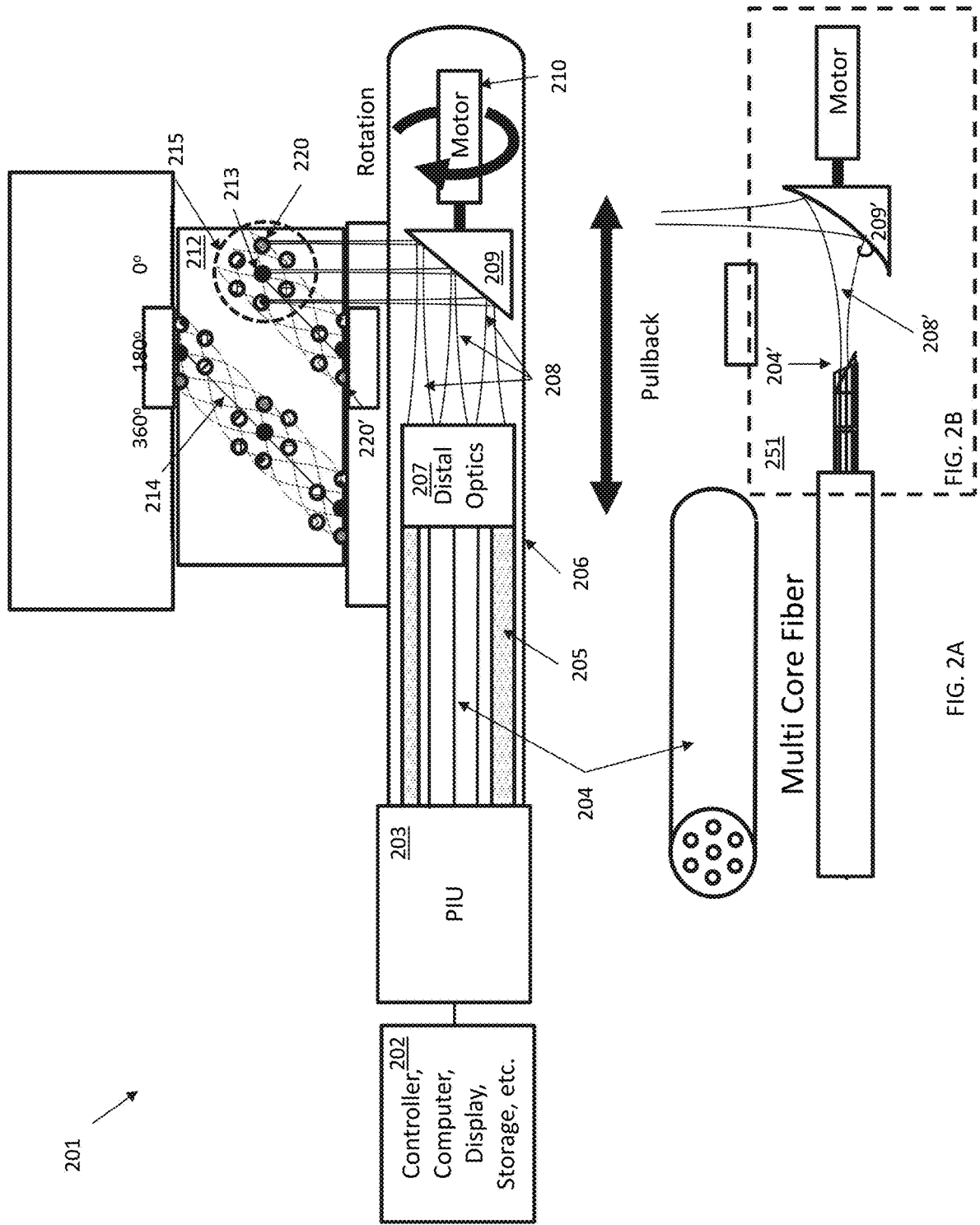
FIG. 2A illustrates an embodiment of an optical probe system with a multicore fiber of the present teaching.
FIG. 2B illustrates an embodiment of a portion of an optical probe system with a non-planar folding element of the present teaching.

In addition to the examples above, there are a wide variety of ways to configure the optical elements in the distal optics element, e.g. distal optics element 107, 207, 307, 407 of FIGS. 2-4, and the relative distance from the distal optical element 107, 207, 307, 407 and the folding element, e.g. folding element 209, 309, 409 of FIGS. 2-4, surface. The surface could be reflective or refractive or wavelength-angularly dispersive (e.g. grating). The surface could be flat or have optical power (e.g. focusing power), and can thereby set the properties of light as it impinges onto the sample (e.g. spot size, depth of field, etc.). The descriptions above just represent a few of the many embodiments of optical probe system that include multicore fibers of the present teaching.

Some of the above description has focused on light emanating from one core being directed toward the sample and retro reflected back into that same core. This is common in known conventional OCT embodiments. But it should be understood that it is also possible to have light start from one core and return in a different core and/or multiple cores. Such approaches can be used in OCT but are even more common in NIR imaging and diffuse wave spectroscopy and other optical imaging modalities. It is also possible to use different wavelengths in any of the embodiments described herein. For example, to emit one wavelength and collect a one or more different wavelengths, as is done is fluorescence or Raman imaging. Multi-wavelength operation can be done in the same core or a different core of the multicore fiber.

Figure 7:
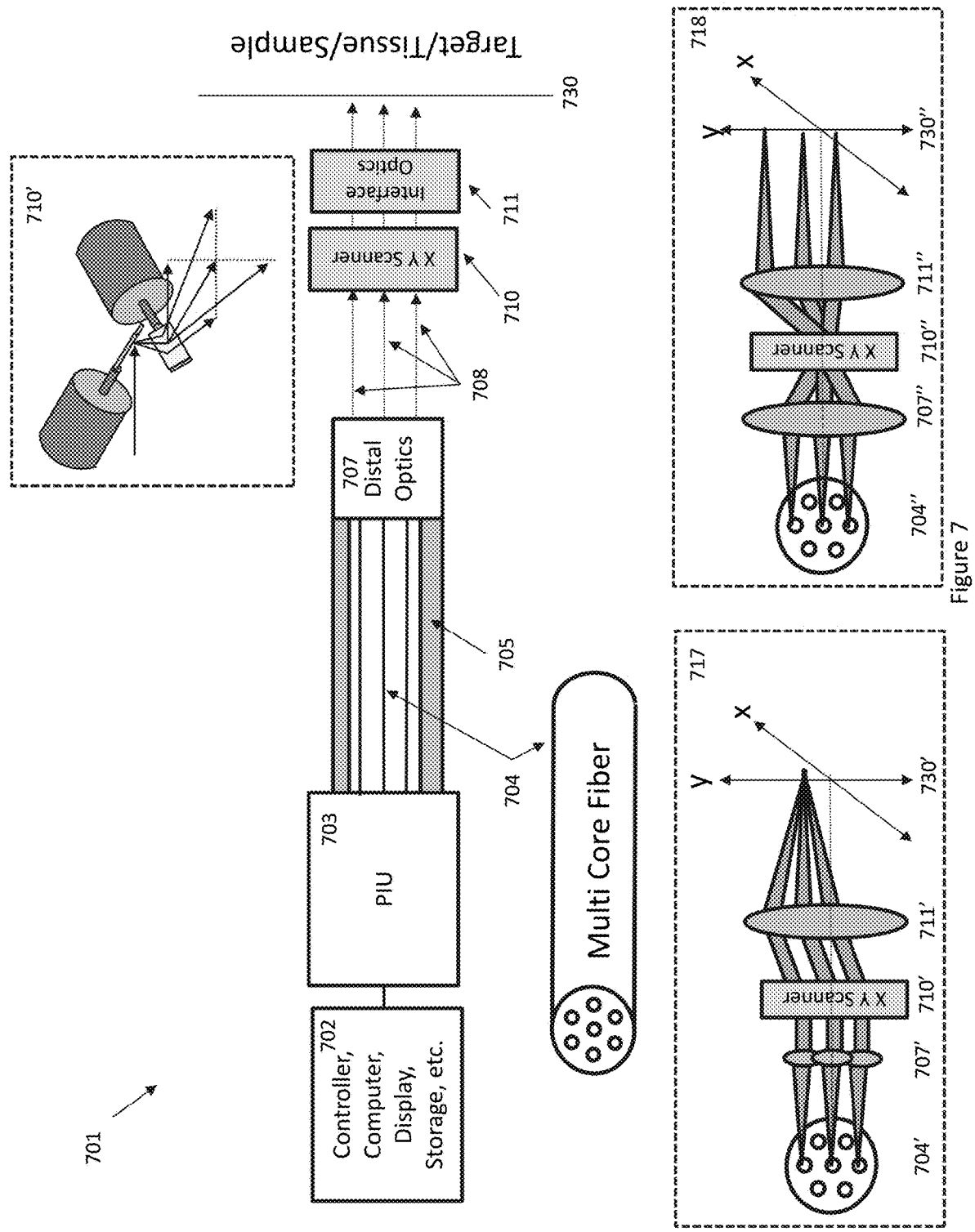
FIG. 7 illustrates an embodiment of an optical probe system with a distal scanner of the present teaching.

FIG. 7 illustrates an embodiment of an optical probe system 701 with a distal scanner 710 of the present teaching. The simplified block diagram of the optical probe system 701 illustrates a forward imaging embodiment for which a multicore fiber 704 is optically coupled to a distal X-Y scanner 710 and optional interface optics 711 that project light to a sample 730. In various embodiments, the sample 730 may be a tissue and/or a target. It should be understood that the term "target" is meant to be a very general term that could be, for example, a car in a LiDAR application or a wide range of other target and application possibilities. Light from a system controller 702 is optically coupled to a multicore optical fiber 704 via PIU 703. In this embodiment, the PIU 703 may be very simple and contain, among other things, a simple multicore fiber optical connector and no pullback mechanism. For example, applications such as ophthalmic imaging or a surgical microscope or more standard microscopy where readily repeated procedure-by-procedure connections are not necessarily needed. In some embodiments, the optical connection is by a fusion splice. In a cardiology or endoscopy applications, PIU 703 may be more complex and configured to support rapid and repeated procedure-by-procedure connections. In some embodiments, the PIU 703 is configured such that a new, and optionally disposable, probe is connected for each procedure.

Only the essential components of optical probe system 701 are shown. For example, some well-known items, such as traditional optical, mechanical, and electrical connections associated with medical and nonmedical instruments are not shown. For example, system 701 could be a spectral domain or swept source domain optical coherence tomography ophthalmic imaging system and the skins, housings, patient chin head rests, alignment adjustments and other items that are well known by those skilled in the art of design and use of commercial OCT systems are not shown in FIG. 7 for simplicity.

The distal optics 707 of the optical probe system 701 can take a variety of forms in different embodiments. For example, there may be no distal optical elements and the light beams from the distal end of multicore fiber 704 propagate toward scanner 710. As another example, lenses and/or other optical elements can be use in the distal optics 707. The lenses and/or other optical elements may be formed using 3D printed optics on the tip of multicore fiber 704. The 3D printed optics may be similar to that discussed previously in connection with FIG. 2A. In some embodiments, the distal optics 707 may take the form of fusion spliced combinations of coreless and graded index multicore fibers, ball lenses, injection molded microlens arrays, and/or other type of single or multi-element lenses or lens arrays. The distal optics 707 transform the optical outputs of the cores of the multicore fiber to be collimated and/or imaged in a suitable way for the particular application. The image is formed in a plane that is positioned between the distal tip of the multicore fiber 704 and the target/tissue/sample 730 indicated by the solid line. Light going from the multicore fiber 704 altered by optional distal optics 707 is illustrated by arrows 708.

The multiple light beams, which are illustrated by arrows 708, are directed to an X-Y scanner 710. There are a variety of types of X-Y scanners 710 that can be used. In one specific embodiment, the X-Y scanner 710 is an X-Y scanning galvanometer that is illustrated in inset illustration 710'. Such galvanometers are in common use in ophthalmic OCT imaging devices. Such galvanometers are also used in various types of microscopes. There are a variety of geometries that can be used to combine two single-axis scanning galvanometers either with, or without, relay lenses between the X and Y mirrors. One- or two-axis PZT, electromagnetic actuator-based devices, MEMs devices, or combinations of devices may also be used to implement the X-Y scanner 710.

The X-Y scanner 710 causes the light pattern to traverse a path across the sample. The scanning transformation of light from a singlecore fiber (which might be the central fiber core of a multicore fiber 704) to the tissue using galvanometers and two axis mirrors is known in the art. Scanning issues, such as pincushion distortion, beam walk between the X and Y galvanometer when they are paired without relay lenses, and angular magnification from scanning are known issues. It is, however, worth noting that, in contrast to the full rotation of the outer cores relative to a central core that was described above (e.g. in connection with the description of FIG. 2A), the rotation resulting from an X-Y scanner 710 is different. For example, the rotation of the cores in pattern 215 illustrated in inset illustration 212 does not occur when using the particular X-Y scanner 710 shown in FIG. 7. Also, the full circular patterns, as shown in either of the inset illustrations 620, 621 of FIG. 6 do not occur when using the X-Y scanner 710. Rather, the scan pattern transformation depends on various factors, such as the geometry of the multicore fiber 704, the configuration of the distal optics 707, the implementation of X-Y scanner 710, the interface optics 711 and other factors. However, the transformation is known a priori and/or can be derived, such that it can be used to transform data collected from a sample using light impinging onto the sample and/or collected from the sample into useful measurement information. Some specific examples of the transformations that can be realized with the X-Y scanner 710 are given below.

One feature of the present teaching is that the multicore fiber with distal motor can be implemented as a microscope optical probe system. In surgical microscopes, colposcopes, anterior chamber ophthalmologic, general microscopy, and other applications it is common to have additional interface optics 711 that are positioned distal to the X-Y scanner 710. In one embodiment, which is illustrated within the dashed box of inset illustration 717, distal optics 707' collimates the individual outputs of each core of multicore fiber 704'. The light passing to and/or from the fiber 704' is directed onto X-Y scanner 710', which may be an X-Y scanning galvanometer. The light is then focused onto to target 730' by interface optics 711'. In this embodiment, the light from the different cores emitted from (or collected into) multicore fiber 704' focuses at roughly the same spot on sample 730' but enters and/or exits from different angles.

As noted earlier, one feature of the present teaching is that it is possible to have light both emitted and collected along the center core of a multicore fiber and also to emit light from the center core and collect light from one or more of the outer cores, or vice versa. For example, referring to FIG. 7, it is possible to have light both emitted and collected along the center core shown in multicore fiber 704, 704', 704" and also light emitted from the center core and collect light from one or more of the outer cores, or vice versa. In general, it is possible to measure one or more combinations of light emitted from a particular core in multicore fiber 704, 704', 704" and then collected from the same or different cores with an N×N matrix of possible input and output patterns. Such information in the matrix of input and output light patterns of the cores can be important indicator of tissue structure as highly scattering tissue is more likely to couple beyond the fundamental back scattered mode as is known in near infrared imaging, OCT, and diffuse wave imaging.

In some embodiments, it is desirable to have the light impinging on a sample at different locations. One approach to accomplish this is illustrated within the dashed box of inset illustration 718. In this embodiment, there is a shared lens 707", which in some embodiments, may be a lens group between the distal facet of multicore fiber 704" and the X-Y scanner 710". If the X-Y scanner 710" is located in a pupil plane (i.e. approximately one focal length in front of the lens 707"), then the light beams will be collimated and will mostly overlap in the X-Y scanner 710". Another lens 711", which in some embodiments is a lens group, can then be used to focus that light into the sample in distinct locations at the target 730".

While inset illustration 717 shows an example where the different beams impinge on the same target location at different angles, and inset illustration 718 shows an example where the different beams impinge on different target locations, there are other embodiments where the different beams impinge on different target locations and also at different angles. That is, combinations of these embodiments are possible, where one or more subsets of cores are configured to overlap and other subsets are configured to impinge at distinct, and/or nonoverlapping locations on the sample. Also, while inset illustration 717 shows the light beams arriving at the X-Y scanner 710' approximately in parallel, and inset illustration 718 shows the light beams arriving at approximately the same spot at the X-Y scanner 710", many other arrangements are possible. For example, the light beams may meet at an X-Y scanner in a diverging pattern or in a converging pattern where the point of convergence is conceptually behind the X-Y scanner. Here again, light beams from different subsets of cores may also be configured to utilize these different patterns.

When the mirrors in the X-Y scanner 710, 710', 710" are moved, the set of target locations and/or set of target angles would also move. Conceptually, the set of different locations and/or angles would typically move as a set, although the extent to which they move as a set, and the details of any distortion or size change or reflection, will depend on various factors, such as the optical elements, the details of the X-Y scanner, and the geometry involved. Known single-core OCT devices can be thought of as corresponding to a center beam (i.e. the beam from the center core of a multicore system), and so the calculations used for known single-core optical probe system can be adapted via a mathematical transformations to apply to the side beams as well.

There are of course a wide variety of other possible combinations of distal optics 707, X-Y scanner 710, and interface optics 711 that can be used. These result in corresponding ways to transfer, image, magnify, and adjust the light from the multicore fiber 704 distal facet to the target 730. In many embodiments, the various optical elements will not be simple single element lenses as shown in FIG. 7 but can be more complex elements including for example, multielement lenses and/or lenses including aspherical elements.

One feature of the multicore fiber with distal motor of the present teaching is that it can be used for imaging of the human eye. FIG. 8 illustrates an embodiment of imaging a human eye 802 using an optical probe system 801 according to the present teaching. FIG. 8 shows light from a multicore optical fiber 804 imaging a human eye 802 where the individual beams sample near the same spot on the retina. Thus, the optical probe system 801 is suitable for imaging within the human eye 802 including the retinal area. Light from multicore fiber 804 is collimated by distal optics 807, and then directed to X-Y scanner 810. Interface optics 811 and 812 are arranged in a relay lens design to relay the optical plane near the center position between the X-Y scanner 810 onto a plane near the pupil of the eye in order to minimize vignetting and maximize light passing through the pupil. The relay lens design also relays the light in a way that the light focuses onto the retina with the desired spot size and corresponding depth of field. As is known by those skilled in the art, the lens properties of the eye (primarily the cornea and lens of the eye) play a strong role in focusing the light impinging on the cornea near the retinal surface. Since the diameter of the human pupil is limited (in both a dilated eye, or an undilated eye), there is a trade-off between the individual beam diameters and the spacing of the beams and the size of the individual spots on the retina. For example, if there is only one fiber core, the beam diameter impinging (or emitted) on to the cornea can fill the pupil and higher lateral spatial resolution can be achieved on the retina. As the number of cores increases, each beam must be reduced to fit within the pupil at the expense of lateral resolution on the retina.

FIG. 9A illustrates another embodiment of imaging a human eye using an optical probe system 901 of the present teaching. In this embodiment, light from a multicore optical fiber 904 images a human eye 902 where the individual beams sample different spots on the retina. Thus, the optical probe system 901 is suitable for imaging within the human eye 902, including the retinal area. The light from the multicore fiber 904 is collimated such that the X-Y scanner 910 is placed in a pupil plane of the fiber facet. In this instance, the term "pupil plane" refers to a plane where the light beams mostly spatially overlap.

There are many ways to optically achieve this pupil plane placement of the X-Y scanner 910 including having the multicore fiber 904 distal facet positioned approximately at the effective back focal length behind lens 907 and the X-Y scanner 910 positioned approximately the effective front focal length in front of lens 907. In this way, the light beams are collimated and impinge and overlap near the effective center of X-Y scanner 910. Interface optics 911 and 912 are arranged to relay the pupil near the center position between X-Y scanner 910 where the light beams spatially overlap onto a plane near the pupil of the eye 902 where again the light beams spatially overlap. There are numerous ways to achieve the relay imaging from the plane of X-Y scanner 910 to the plane of the pupil of the eye 902. The use of the relay lens in the optical probe system 901 has the advantage of allowing each of the light beams from the multicore fiber to overlay in the pupil of the eye 902 and thus allows each light beam to have a wider diameter, as compared, for example, to the diameter of light beams shown in FIG. 8. The wider diameter of the light beams can translate to a smaller spot size on the retina and thus higher lateral spatial resolution (and better use of available optical signal power). In the embodiment of FIG. 9, the center of spots does not overlap on the retina. As such, it is possible to have relatively fast imaging time as the scan can cover more area due to multiple receivers running in parallel each sampling a different area on the retina.

The embodiment of the multicore fiber with distal motor FIG. 9 has similar features of the embodiment shown in inset illustration 718 of FIG. 7. In both these embodiments, the multiple light beams from the multiple cores impinge on multiple (different) target locations, thereby allowing faster scanning, either with multiple parallel receivers or a fast-switched system, which is described further herein. The target plane 730 shown in inset illustration 718 can be identified with a conceptual "intermediate" plane between optical elements 911 and 912 and the optical element 912 and lens properties of the human eye 902 together translates this intermediate plane onto the retina. The "intermediate" plane is conceptually indicated by the X-Y axes 913 shown in FIG. 9. As described herein, when the mirrors in the X-Y scanner 910 are moved, the beams will typically move as a set on this intermediate plane, which therefore means they also typically move as a set on the retina. Also as described herein, the extent to which they move as a set, and the details of any distortion or size change or reflection, will depend on the optical elements, the details of the X-Y scanner 910, the geometry involved, and, in case of the optical probe system 901 embodiment of FIG. 9, the properties of the human eye 902.

In one embodiment, the X-Y scanner 910 is programmed to perform a row-by-row scan of a desired target area of the retina. FIG. 9B illustrates a single-core, row-by-row scan pattern. FIG. 9C illustrates the loci of the seven different target spots in a multi-core OCT system in such a row-by-row scan. As shown, the coverage of the target area is much greater than in the single-core case of FIG. 9B. Alternatively, for the single-core case to achieve similar coverage would require many more rows in the scan, which translate into a much slower scan. In the example shown in FIG. 9C, the loci overlap, which means some retina locations are scanned multiple times (by different beams) at different times, which allows averaging to improve image quality, detection of motion via speckle decorrelation, etc.

In applications where overlapping of loci is considered undesirable (i.e. any added benefit does not justify the added systems costs), a multi-core fiber with only cores A, B, C (or only cores A, B, C, D, E) can be used, to minimize overlap (and potentially system cost). Alternatively, FIG. 9D shows a slightly different situation where the seven target locations are slightly rotated, in such a way that their loci overlap much less during the row-by-row scan.

While the scan patterns of FIGS. 9B-D cover conceptual examples of row-by-row scanning, other scanning patterns (raster, serpentine, spiral, Lissajous, etc.) can be utilized. When other scanning patterns are utilized, similar calculations of a number of cores, core geometry, overlap, and coverage efficiency are applied. There are a wide variety of types of multicore fiber in addition to the seven-core example shown in FIG. 9 including 1×N geometries (linear arrays), triangular patterns, circular patterns, and many others.

One aspect of the multicore fiber with distal motor of the present teaching is the use of parallel spectral domain or swept source domain optical coherence tomography receivers with receiver components integrated on a shared integrated photonic circuit with a multicore optical fiber and an imaging arrangement. One such configuration can be similar to that shown in FIG. 9, which allows multiple beams emitted from (or collected) into a multicore fiber where there is a distal X-Y scanner, and optics are configured to allow multiple near collimated beam to overlap in part as they pass through the pupil of a human eye and focus to different spots on the human retina. One advantage of parallel receivers, for example parallel OCT receivers, is it allows more rapid scanning of tissue area.

Figure 10:
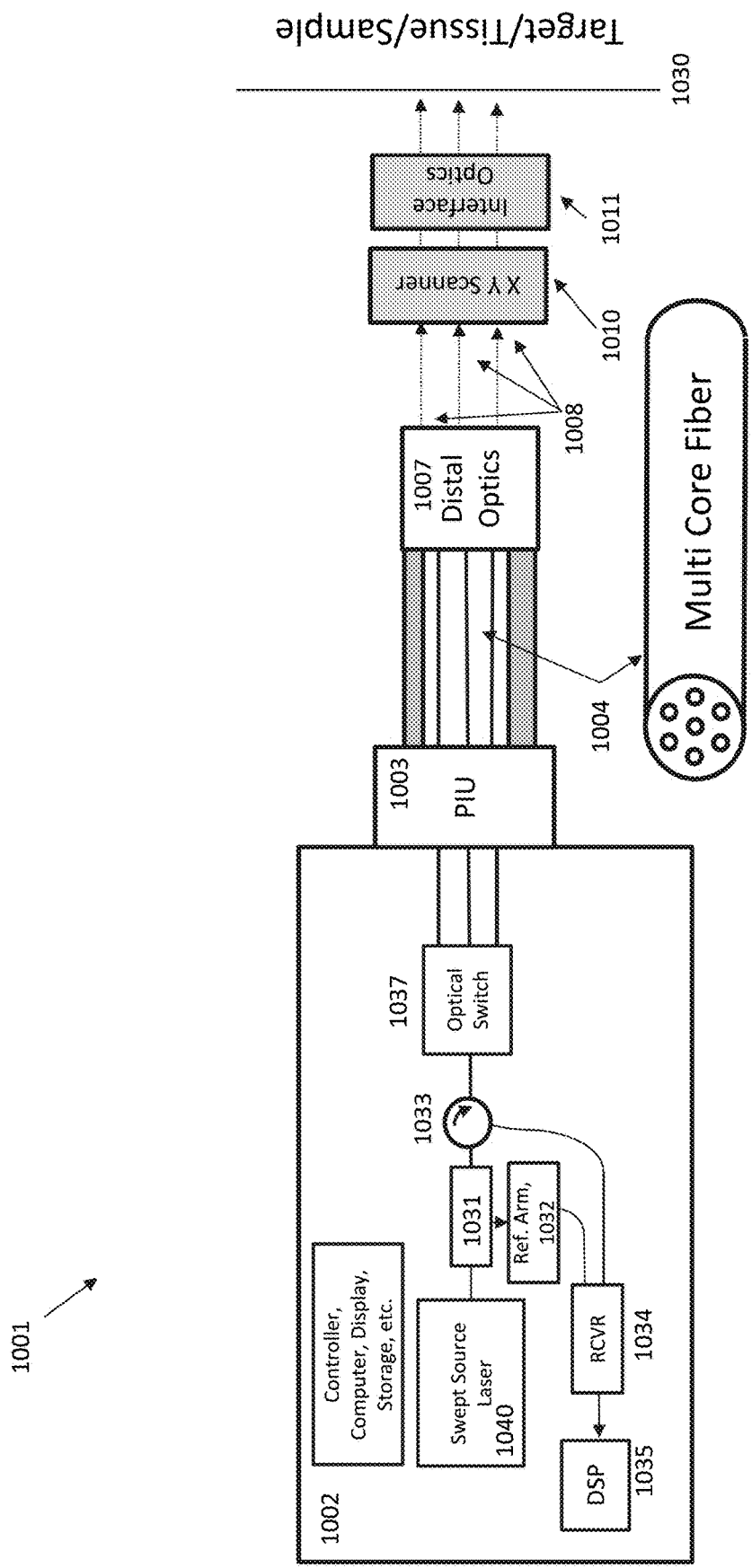
FIG. 10 illustrates an embodiment of an optical probe system including and X-Y scanner and optical switch of the present teaching.

Some embodiments of the present teaching utilize a fast optical switch to select optical beams. FIG. 10 illustrates an embodiment of an optical probe system 1001 including and X-Y scanner 1010 and an optical switch 1037 of the present teaching. The optical probe system 1001 includes a control system 1002 that includes the optical switch 1037 and is connected to PIU 1003. The PIU 1003 interfaces to a multicore fiber 1004, distal optical 1007, optical scanner 1010, interface optics 1011, and to target 1030. In the control system 1002, the optical switch 1037 allows a single receiver 1034 and DSP 1035 to receive and process optical beams selected from different cores of multicore fiber 1004.

There are many ways to implement the fast-optical switch 1037. For example, a photonic integrated circuit (PIC) switch using a Mach Zehnder or other PIC switch topologies, LiNbO3 switches, and others may be used. The rate at which swept source lasers can scan can be very high. In some embodiments, the laser source 1040 can sweep much faster than the X-Y scanner 1010 can scan. As such, by having a fast-optical switch, it is possible to have a simpler and lower cost structure for receiver 1034 and still sample multiple tissue spots. This is in contrast to the embodiment described in connection with FIG. 3 where the output power can be shared among the cores of the multicore fiber and the receivers collect light in parallel.

In the optical probe system 1001 of FIG. 10, all the transmit light is sent to one core of multicore fiber 1004, and the signal from that core is collected. Then, the optical switch 1037 switches to the next core of multicore fiber 1004 and the process is repeated. Thus, the optical switch 1037 is configured so the switching rate of the switch 1037 is synchronized to the collection rate of light from each core being received by the receiver 1034. During this process, the X-Y scanner 1010 can continue to scan. The swept source laser 1040 repetition rate is coordinated with the switching rate of the optical switch 1037 to ensure that the transitions of the laser 1040 and switch 1037 are synchronized and the full sweep of the source 1040 is completed when the switch 1037 has completed its connection. Light from the swept source 1040 is coupled to splitter 1031. The splitter 1031 directs part of the light to a reference arm 1032. The reference arm 1032 may include a variable delay to assist in matching the lengths between the sample arm and the reference arm as is known in the art of OCT.

Another part of the output of the splitter 1031 is sent to a circulator 1033 and then to the optical switch 1037, which is connected to PIU 1003. An output of the circulator is connected to receiver 1034. The multicore fiber 1004, distal optics 1007, optical beams 1009, X-Y scanner 1010, optional interface optics 1011, and target 1030 are similar to those described in the earlier figures. Back reflected light from the target 1030 is coupled into the interferometric receiver 1034 and processed by DSP 1035 to extract information about the target (e.g. range, morphology, dimensions, birefringence, absorption, scattering, etc.).

In one embodiment, the optical source 1040 and the optical switch 1037 are integrated onto a single photonic integrated circuit. In another embodiment, parts of the optical receiver 1034 and the optical switch 1037 are integrated onto a single photonic integrated circuit. Both approaches for photonic integration have advantages, chief among them is that tight physical integration and small size make synchronization between scanning of the imaging and switching of the switch easier and achieve lower costs.

Although the embodiment of optical probe system 1001 shown in FIG. 10 was described in terms of a swept source OCT system it should be understood that it is equally applicable to spectral domain OCT system and other types of optical systems such as NIR, fluorescence, Raman, diffuse wave, and other optical imaging and sensing systems.

APPENDIX

This appendix presents relevant mathematical details of the path traced by a optical sample spot such as 220 and 220' in FIG. 2A. We solve here the cases of FIG. 2 and FIG. 4 explicitly. While we only solved these two cases, it is straightforward to those skilled in the art that the analysis can be easily generalized to other embodiments. For example, the application to different mirror angles, other beam angles, other physical distances, multicore fiber geometries, motions and other design parameters is straightforward.

Note that in reality, optical spot 220 has a non-zero size because optical beam 208 has a non-zero width. This description in this appendix mostly relates to the location of the spot, not its size, and especially relates to how the location changes as the mirror rotates. The appendix describes details of the path traversed by an optical sample spot as a function of the motion provided by the probe. Accordingly, the appendix idealizes the spot as a single dimensionless point (i.e. zero size), and the beam as a 1-dimensional line or ray (i.e. zero width). An alternative and equivalent view is that this appendix solves for the location of the "center" of the actual optical spot, illuminated by the "chief" or "central" ray of the actual beam. In this appendix, the words "spot" and "beam" and the like will usually refer to their idealized versions. The extension to include finite size optical sample spots with varying size, shapes and/or relative positions is straightforward.

A.1 Mirror Frame and Basic Equations

Consider a three-dimensional reference frame with the origin being the fixed point on the mirror which does not rotate. This frame is referred to herein as "the mirror frame". The z axis is positioned along the direction of pullback, with +z being the direction from the distal optics toward the mirror, and the x axis and y axis defined according to the usual right-hand rule. Note that there is a slightly different geometry than the geometry shown in FIG. 1, 111, where +z is in the other direction.

The center core has coordinates $(x, y, z) = (0, 0, p)$ where $p<0$ and $|p|$ is the distance from the center core at the end of the distal optics to the mirror center. A typical new "side" core will have coordinates $(x, y, z) = (a, b, p) = (r \cos \phi, r \sin \phi, p)$ where $(a, b)$ or equivalently $(r, \phi)$ represents its position with respect to the center core. Thus, the relative position of at least two cores at the distal facet of the multicore fiber corresponds to the mathematical mapping of the path traced by optical sample spots in a light pattern generated by the multicore fiber in the optical probe.

For the configurations shown in FIG. 2A (and ignoring at this point the effects of distal optical element 207), the beam leaves the core and travels in the +z direction, represented by the vector (0, 0, 1). The equations for the beam are therefore: $x=a$, $y=b$, with z being unconstrained. We will call the beam from the fiber to the mirror the incident beam, and the beam from the mirror to the lumen the reflected beam.

The mirror surface is described by its perpendicular vector N=(c, s, t) where for shorthand we write c=cos θ, s=sin θ; θ=the instantaneous angle of the rotating mirror; and t=represents the tilt of the mirror.

The angle between N and the +z axis is given by angle A where cos $A = N \cdot (0,0,1)/|N| = t/\sqrt{c^2+s^2+t^2} = t/\sqrt{t^2+1}$. In the case of FIG. 2A, A=135° and t=−1.

Given the vector N and the fact that the mirror (by convention) passes through the origin, the equation for the mirror surface is N·(x, y, z)=cx+sy+tz=0.

A.2 Point of Reflection and Direction of Reflection

The beam hits the mirror at the intersection of all the equations, i.e. x=a, y=b, cx+sy+tz=0 or z=−(ca+sb)/t.

Let F and D be the unit-length vectors describing the direction of the incident beam and the reflected beam, respectively. (For example, F=(0, 0, 1) in case of FIG. 2A.) Then, the following equation holds: $D-F=2(-F \cdot N)N/|N|^2$ where N is the (not necessarily unit-length) perpendicular vector of the mirror surface. Solving this for FIG. 2A, we have $$D=(0,0,1)-2tN/(t^2+1)=(-2tc/(t^2+1),-2ts/(t^2+1),1-2t^2/(t^2+1))$$

Note that the x and y components of D are proportional to (c, s) which verifies the obvious fact that the incident beam, the vector N, and the reflected beam are all in the same rotational plane described by θ. Also note that for the configuration shown in FIG. 2A where t=−1 (i.e. A=135°), we have D=(c, s, 0) representing a 90° turn as expected.

A.3 where the Reflected Beam Hits the Lumen

The lumen is modeled as an enclosing cylinder, centered at the origin, aligned along the z direction, with radius R. The equation for the cylinder is $x^2+y^2=R^2$ (with z unconstrained).

Note that, in reality, the lumen is only approximately a cylinder, and indeed the fine structure of the lumen (including potentially depth structure) is usually what is being measured. This appendix models the lumen as a cylinder because it is mainly concerned with the location where the beam hits the (idealized) cylinder, as measurements at this location reveal the fine structure (including potentially depth structure) of the lumen at this location.

The reflected beam is fully characterized by its point on the mirror (a, b, −(ca+sb)/t) and its direction D. For the case of FIG. 2A, since t=−1 and D=(c, s, 0), the reflected beam is described by the parametrized position (a+uc, b+us, ca+sb) where u is a free (positive) parameter. This beam hits the lumen at the point, which we will call the "contact point", where $$R^2=(a+uc)^2+(b+us)^2=u^2+u(2ac+2bs)+(a^2+b^2)$$

This is a quadratic equation in u which can be solved exactly to find the illuminated point. An equivalent, and more intuitive, characterization uses (a, b)=(r cos φ, r sin φ) and the quadratic equation becomes:

$$R^2=u^2+2ru \cos(\phi-\theta)+r^2=u^2+2ru \cos \Delta+r^2$$

where we introduced the shorthand variable Δ=φ−θ. Solving this quadratic explicitly, we have $u=\sqrt{R^2-r^2\sin^2\Delta}-r \cos \Delta$.

A.4 The "Unwrapped" Cylinder

The equations in the previous sections (A.1-A.3) are all exact, and they give the exact point in three-dimensional space where the reflected beam contacts or illuminates the lumen. That is, these equations detail the path traversed by an optical sample spot as a function of the motion provided by the probe. However, it is customary in the art (and often convenient for displaying information) to consider the "unwrapped" cylinder (sometimes known as en face view) and the locus of the contact point in this unwrapped cylinder.

The unwrapped cylinder is defined by cutting the cylinder open at all points where x=+R and then flattening it into a 2-dimensional space, characterized by two parameters: z and β, the angle (in the (x, y)-plane) with respect to the original cylinder. That is, a point (z, β) in the unwrapped cylinder is equivalent to the point (R cos β, R sin β, z) in the 3-D frame.

Note that it is sometimes customary in the art to use Rβ, a distance along the cylinder circumference, instead of β as the second parameter. For this equivalent characterization, β should be measured in radians.

The contact point's exact location in 3-D space can be mapped to its exact location in the (z, β) or (z, Rβ) view by equating (a+uc, b+us, ca+sb)=(R cos β, R sin β, z). In particular:

$$z=ca+sb=r \cos \Delta$$

However, the resulting formula for β is cumbersome. Certain approximations greatly simplify the formula and provide helpful insight for those skilled in the art to understand and optimize the inventions describe here in a wide variety of medical and non-medical applications.

A.5 Helpful Approximations for β

In this analysis, some approximations are made to simply the calculations. In a first approximation: Typically R>>r (i.e. the lumen radius is much greater than the distance between a side core and the center core of the fiber). Thus we have:

$$u=\sqrt{R^2-r^2\sin^2\Delta}-r \cos \Delta \approx R(1-r^2 \sin^2\Delta/2R^2)-r \cos \Delta \approx R-r \cos \Delta$$

where we have kept any r/R term but dropped all $(r/R)^2$ and higher order terms.

As is well known in the art, for the single-core case β=θ, i.e. the beam hits the lumen at exactly the instantaneous angle of the rotating mirror. For a side core, we model its angle β as a perturbation β=θ+α.

In a second approximation 2: since α is a small angular perturbation, we have cos α≈1, sin α≈α, where we have kept any α term but dropped all $\alpha^2$ and higher order terms.

Both approximations can be considered "linearizing" approximations, since they keep small linear terms but ignore even smaller quadratic and higher order terms. Using these two approximations, we now equate the x and y components. For instance, equating the x component R cos(θ+α)=α+uc and using Approximation 1, we have:

$$R\cos\theta\cos\alpha - R\sin\theta\sin\alpha \approx r\cos\phi + (R - r\cos\Delta)\cos\theta$$
$$= r\cos\phi + R\cos\theta - r\cos\theta(\cos\theta\cos\phi + \sin\theta\sin\phi)$$
$$= R\cos\theta + r\cos\phi\sin^2\theta - r\cos\theta\sin\theta\sin\phi$$
$$= R\cos\theta - r\sin\theta\sin\Delta$$

Now the second approximation allows us to identify Rα≈R sin α≈r sin Δ=r sin(φ−θ).

Equating they components, R sin(θ+α)=b+us, and using the same approximations, lead to the same results.

In summary, in the (z, Rβ) view, the contact point is (r cos Δ, Rθ+r sin Δ), with the above approximations. This means that, as the mirror rotates (θ changes), while the reflected center core beam's contact point moves simply according to Rθ (as is known in prior art), the reflected side core beam's contact point rotates around the center beam's contact point, in a circle of radius r and rotating according to the angle $\Delta=\phi-\theta$.

A.6 Pullback

So far, we have described the geometric equations in a frame attached to the mirror. In practice, of course, the mirror (the whole capsule/apparatus) moves within and along the lumen or natural mechanical fixture guiding it. This can be easily handled by redefining the z=0 reference to be a fixed point along the lumen instead of the fixed point on the mirror. For example, if the capsule is pulled back at constant speed v, then the reflected center core beam's contact point is now $(z_0-vT, R\theta)$ where T is time, and the reflected side core beam's contact point is now $(z_0-vT+r \cos \Delta, R\theta+r \sin \Delta)$, i.e., it still rotates around the reflected center core beam's contact point, $(z_0-vT, R\theta)$. Note that typically the mirror also rotates at constant angular velocity, e.g. $\theta=\omega T$, thereby giving the reflected side core beam's contact point as $(z_0-vT+r \cos(\phi-\omega T), R\omega T+r \sin(\phi-\omega T))$. This is illustrated in FIG. 2A, illustration 212.

A.7 Exact Geometry of FIG. 4

The preceding sections (A.1-A.6) show a detailed solution for the case of FIG. 2A, where the incident beam is in the +z direction, i.e. (0, 0, 1). We now briefly solve the case of FIG. 4, where each incident beam is aimed to hit the mirror at the origin. In practice, this allows a very small mirror, which in turn may allow higher angular velocity due to relaxed mechanical constraints, and the endoscope to fit into even small lumens or access ports of medical or non-medical instruments.

The incident beam goes from (a, b, p) to (0,0,0) so the unit-vector for its direction is F=−(a, b, p)/k where k=$\sqrt{a^2+b^2+p^2}=\sqrt{r^2+p^2}$ is the normalizing factor. The unit-vector for the reflected beam is:

$$D=F-2(F \cdot N)N/|N|^2$$

As before, N=(c, s, t) is the perpendicular vector for the mirror surface.
Therefore:

$$D=\{-(a,b,p)+2(ac+bs+pt)(c,s,t)/(t^2+1)\}/k$$

Note that ac+bs=r cos $\Delta$. Also, for the configuration shown in FIG. 4, the tilt angle between N and +z axis is A=135° and t=−1. Therefore, the above simplifies slightly to:

$$D=\{-(a,b,p)+(r \cos \Delta - p)(c,s,-1)\}/k$$

$$kD=(X,Y,-r \cos \Delta)$$

where for convenience, we define X=(r cos $\Delta$−p)c−a and Y=(r cos $\Delta$−p)s−b.

As before, the reflected beam can be parametrized by u. Since u is a free (positive) variable, it does not matter whether we include or exclude the positive rescaling factor k. Since the reflected beam originates from the origin (where the incident beam hits the mirror), the reflected beam is simply ukD. The contact point where the reflected beam hits the lumen is given by:

$$R^2=x^2+y^2=u^2\{X^2+Y^2\}$$

We can solve for the exact value of u as follows:

$$X = (r\cos\Delta - p)c - a = \cos\theta\{r(\cos\theta\cos\phi + \sin\theta\sin\phi) - p\} - r\cos\phi$$
$$= r\sin\theta\cos\theta\sin\phi - r\cos\phi\sin^2\theta - p\cos\theta$$
$$= r\sin\theta\sin\Delta - p\cos\theta$$

$$Y = (r\cos\Delta - p)s - b = \sin\theta\{r(\cos\theta\cos\phi + \sin\theta\sin\phi) - p\} - r\sin\phi$$
$$= r\sin\theta\cos\theta\cos\phi - r\sin\phi\cos^2\theta - p\sin\theta$$
$$= -r\cos\theta\sin\Delta - p\sin\theta$$

$$X^2 = r^2\sin^2\theta\sin^2\Delta - 2rp\cos\theta\sin\theta\sin\Delta + p^2\cos^2\theta$$

$$Y^2 = r^2\cos^2\theta\sin^2\Delta + 2rp\sin\theta\cos\theta\sin\Delta + p^2\sin^2\theta$$

$$X^2 + Y^2 = r^2\sin^2\Delta + p^2$$

$$u = R/\sqrt{p^2 + r^2\sin^2\Delta}$$

So the exact 3-D location of the contact point ukD=R (X, Y, −r cos $\Delta$)/$\sqrt{p^2+r^2\sin^2\Delta}$. In particular, the z component is:

$$z=-Rr \cos \Delta/\sqrt{p^2+r^2\sin^2\Delta}$$

This value is different from the value in FIG. 2A, which is described more in connection with A4 in two ways. First there is a rescaling factor of u=R/$\sqrt{p^2+r^2\sin^2\Delta}$, and second, there is a negative sign. Both will be explained more fully in the next section.

A.8 Approximations for FIG. 4 and the Unwrapped View

As before, we now map the exact 3-D location onto the unwrapped view characterized by (z, R$\beta$) and as before, some approximations will greatly help with intuitive understanding.

In a third approximation, since the mirror surface is at 45°, we must have |p|>r or else the incident beam would be behind the mirror surface. In practice, we often have |p|>>r. Therefore, once again we will "linearize" the model and ignore any $(r/|p|)^2$ and higher order terms. This allows us to simplify $\sqrt{p^2+r^2\sin^2\Delta}\approx\sqrt{p^2}=|p|=-p$ (recalling that p is negative by convention), and as a result, u≈R/|p|.

Using this approximation, we have z≈−Rr cos $\Delta$/|p|.

Next we equate the x component, and use the second approximation:

R cos $\beta$=R cos($\theta+\alpha$)=R cos $\theta$ cos $\alpha$−R sin $\theta$ sin $\alpha$≈R cos $\theta$−R$\alpha$ sin $\theta$=uX≈R(r sin $\theta$ sin $\Delta$−p cos $\theta$)/|p|=R cos $\theta$+Rr sin $\theta$ sin $\Delta$/|p|

This allows us to identify R$\alpha$=−Rr sin $\Delta$/|p|.

For completeness, we now equate the y component with the same approximations:

$$R\sin\beta = R\sin\theta\cos\alpha + R\cos\theta\sin\alpha \approx R\sin\theta + R\alpha\cos\theta =$$
$$uY \approx R(-r\cos\theta\sin\Delta - p\sin\theta)/|p| = R\sin\theta - Rr\cos\theta\sin\Delta/|p|$$

which again allows us to identify R$\alpha$≈−Rr sin $\Delta$/|p|.

In summary, in the (z, R$\beta$) view, the contact point is (−Rr cos $\Delta$/|p|, R$\theta$−Rr sin $\Delta$/|p|), with the above approximations. This means that, as the mirror rotates ($\theta$ changes), while the reflected center core beam's contact point moves simply according to R$\theta$ (as is known in prior art), the reflected side core beam's contact point rotates around the center beam's contact point, in a circle of radius Rr/|p| and rotating according to the angle $\Delta=\phi-\theta$.

Referring to FIG. 2A, which was described in connection with A.4-A.5, the radius of rotation of the contact point is no longer r, but instead is Rr/|p|. This can be best described by visualizing the "cone" formed by the incident beams from the multiple side cores. This cone has a base of radius r, and has its apex at the origin which is distance |p| away, with an apex angle=2 arctan(r/|p|). The reflected beams also form a cone with its apex at the origin, with the same apex angle.

Therefore, as the reflected cone hits the lumen which is approximately distance R away, the projection onto the lumen is an approximately circular base of radius rescaled by a factor of R/|p|, i.e. a radius of Rr/|p|. In summary, the two cones are similar in the geometric sense (subject to the approximations).

Mathematically, the contact point of FIG. 2A and the contact point of FIG. 4 are exactly half a circle apart, as evidenced by the minus signs in (−Rr cos Δ/|p|, Rθ−Rr sin Δ/|p|). However, this does not materially affect the efficacy of either embodiment, as such sign changes will be handled by the proximal unit's computations.

Sections A.7-A.8 use the mirror frame. Similar to section A.6, pullback of the FIG. 4 scenario (i.e. movement with respect to the lumen frame), can again be easily incorporated as $(z_0-vT-Rr \cos \Delta/|p|, R\theta-Rr \sin \Delta/|p|)$, or by assuming $\theta=\omega T$, as $(z_0-vT-Rr \cos(\phi-\omega T)/|p|, R\omega T-Rr \sin(\phi-\omega T)/|p|)$.

A.9 Concluding Remarks on the Mathematical Treatment in this Appendix

Section A.1-A.6 solved the configuration described in connection with FIG. 2A, with incident beams in the +z or (0,0,1) direction. Section A.7-A.8 solved the configuration described in connection with FIG. 4, with incident beams converging at the origin. While the exact 3-D solutions for the contact points are described, the exact solutions are cumbersome. The approximate unwrapped view gives a much more intuitive picture of the side contact points rotating around the center contact point, while the center contact point traces an (unwrapped) line in the (z, Rβ) view. These are illustrated in FIGS. 2 and 4 respectively.

If the incident beams are at some other angles, the equations in this appendix can be modified to describe them, and similar approximations can be used to understand them intuitively. However, an even simpler approximate understanding can be obtained if we simply view the mirror, not as reflecting the incident beams, but as providing virtual beam sources behind the mirror that shine through the mirror. For example, if the incident beams are start at z-distance |p| away as usual and converge at a point z-distance q in front of the mirror, then by considering the two similar cones from the virtual sources, through the convergence point, to the contact points on the lumen, we again have two similar cones (subject to approximations). Referring to FIG. 4, the relative "heights" of the cones are |p|: R. In the new example, the relative "heights" will be (|p|−|q|):(R+|q|). As a result, the side core beam's contact points will still (approximately) rotate around the center core beam's contact point, but now with a radius of (R+|q|)r/(|p|−|q|).

Similarly, if the incident beams converge at a point z-distance q' behind the mirror, the new radius of rotation for the side core beams' contact points will be (R−|q'|)r/(|p|+|q'|), provided R>|q'|. Cases of R<|q'| or cases of the incident beams diverging can be similarly handled by considering basic geometry using the virtual sources. Indeed FIG. 2A is the special case of the incident beams neither converging nor diverging and equivalent to taking q'=+∞.

As long as the mirror surface is 45° (angle A=135° and tilt t=−1), the circle formed by the virtual beam sources and the circle formed by the real beam sources (at the end of the fiber/optics) will be perpendicular, which means the reflected beam cone will be perpendicular to the z-axis. However, if the mirror surface is not 45° (tilt t≠−1), then the two circles will no longer be perpendicular. In this case the reflected beam cone will not be perpendicular to the z-axis, and the projection onto the lumen (in the unwrapped view) will be approximately an ellipse instead of approximately a circle. However, the side core beams' contact points will still rotate around center core beam's contact point, although in an (approximately) elliptical circuit.

In summary, although FIG. 2A and FIG. 4 are sample embodiments, the analysis in this appendix can be extended to include other lengths and other beam angles and mirror angles

EQUIVALENTS

While the Applicant's teaching is described in conjunction with various embodiments, it is not intended that the Applicant's teaching be limited to such embodiments. On the contrary, the Applicant's teaching encompasses various alternatives, modifications, and equivalents, as will be appreciated by those of skill in the art, which may be made therein without departing from the spirit and scope of the teaching.

What is claimed is:

1. An optical probe imaging system comprising:
   a) an optical probe;
   b) a multicore optical fiber positioned in the optical probe and having a proximal and a distal end;
   c) distal optics that are optically coupled to the distal end of the multicore optical fiber, the distal optics imaging light propagating in the multicore optical fiber so as to generate a light pattern on a sample that is based on a relative position of at least two cores at a distal facet of the multicore optical fiber;
   d) a distal motor mechanically coupled to the optical probe so that a motion of the distal motor causes the light pattern to traverse a path across the sample;
   e) an optical receiver having an input that is optically coupled to the proximal end of the multicore optical fiber, the optical receiver comprising a first receiver configured to receive light that has traversed the path across the sample from one of the at least two cores and a second receiver configured to receive light that has traversed the path across the sample from the other of the at least two cores, such that the first receiver and the second receiver detect light in parallel, the optical receiver generating an electrical signal corresponding to the received light; and
   f) a processor having an input coupled to an output of the optical receiver, the processor mapping the electrical signal to a representation of information about the sample, wherein the mapping is based on the relative position of at least two cores at the distal facet of the multicore fiber and on the motion of the distal motor.

2. The optical probe imaging system of claim 1 wherein the relative position of at least two cores is such that a spot from one of at least two cores and a spot from the other of at least two cores visits a nominally same position at the sample at different times.

3. The optical probe imaging system of claim 1 wherein the distal motor includes a galvanometer.

4. The optical probe imaging system of claim 1 wherein the distal motor is an X-Y scanner.

5. The optical probe imaging system of claim 4 wherein the X-Y scanner is configured such that light impinges on a sample at two different locations.

6. The optical probe imaging system of claim 4 wherein the X-Y scanner is configured such that the light pattern overlaps at least in part across the sample.

7. The optical probe imaging system of claim 1 wherein the optical probe imaging system is an optical coherence tomography system.

8. The optical probe imaging system of claim 1 wherein the optical receiver includes a photonic integrated circuit.

9. The optical probe imaging system of claim 8 wherein the photonic integrated circuit comprises a plurality of optical receivers.

10. The optical probe imaging system of claim 9 wherein the optical probe imaging system is an optical coherence tomography system.

11. The optical probe imaging system of claim 8 wherein the photonic integrated circuit comprises a plurality of optical receivers on a single photonic integrated circuit.

12. The optical probe imaging system of claim 8 wherein the optical probe imaging system is an optical coherence tomography system.

13. The optical probe imaging system of claim 1 further comprising an optical switch optically coupled to the proximal end of the multicore fiber.

14. The optical probe imaging system of claim 13 wherein a switching rate of the optical switch is synchronized to a collection rate of received light by the receiver.

15. The optical probe imaging system of claim 13 wherein the optical switch includes a photonic integrated circuit.

16. The optical probe imaging system of claim 1 further comprising an optical source having an output that is coupled to the proximal end of the multicore optical fiber.

17. The optical probe imaging system of claim 16 wherein the optical source is a swept optical source and the optical receiver is a swept source domain optical coherence tomography receiver.

18. The optical probe imaging system of claim 1 wherein the distal end of the multicore fiber is formed with an angled distal facet that reduces back reflection.

\* \* \* \* \*